US011725218B2

(12) United States Patent
Doyon et al.

(10) Patent No.: US 11,725,218 B2
(45) Date of Patent: *Aug. 15, 2023

(54) ARTIFICIAL NUCLEASES COMPRISING ENGINEERED CLEAVAGE HALF-DOMAINS

(71) Applicant: Sangamo Therapeutics, Inc., Brisbane, CA (US)

(72) Inventors: Yannick Doyon, Brisbane, CA (US); Jeffrey C. Miller, Brisbane, CA (US)

(73) Assignee: Sangamo Therapeutics, Inc., Brisbane, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/493,655

(22) Filed: Oct. 4, 2021

(65) Prior Publication Data
US 2022/0145307 A1     May 12, 2022

Related U.S. Application Data

(63) Continuation of application No. 16/838,804, filed on Apr. 2, 2020, now Pat. No. 11,136,599, which is a continuation of application No. 16/055,525, filed on Aug. 6, 2018, now Pat. No. 10,640,790, which is a continuation of application No. 15/660,072, filed on Jul. 26, 2017, now Pat. No. 10,066,242, which is a continuation of application No. 15/160,571, filed on May 20, 2016, now Pat. No. 9,765,361, which is a continuation of application No. 14/627,812, filed on Feb. 20, 2015, now Pat. No. 9,376,689, which is a continuation of application No. 12/931,660, filed on Feb. 7, 2011, now Pat. No. 8,962,281.

(60) Provisional application No. 61/337,769, filed on Feb. 8, 2010, provisional application No. 61/403,916, filed on Sep. 23, 2010.

(51) Int. Cl.
| | |
|---|---|
| *C12N 15/90* | (2006.01) |
| *C12N 9/22* | (2006.01) |
| *C12N 9/10* | (2006.01) |
| *C12N 15/52* | (2006.01) |
| *C12N 15/85* | (2006.01) |
| *C07K 14/47* | (2006.01) |
| *C07K 7/06* | (2006.01) |

(52) U.S. Cl.
CPC ............ *C12N 15/907* (2013.01); *C07K 7/06* (2013.01); *C07K 14/47* (2013.01); *C12N 9/10* (2013.01); *C12N 9/22* (2013.01); *C12N 15/52* (2013.01); *C12N 15/85* (2013.01); *C07K 2319/50* (2013.01); *C07K 2319/80* (2013.01); *C07K 2319/81* (2013.01); *C12Y 301/21004* (2013.01)

(58) Field of Classification Search
None
See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,200,759 B1 | 3/2001 | Dove et al. | |
| 6,453,242 B1 | 9/2002 | Eisenberg et al. | |
| 6,503,717 B2 | 1/2003 | Case et al. | |
| 6,534,261 B1 | 3/2003 | Cox et al. | |
| 6,599,692 B1 | 7/2003 | Case et al. | |
| 6,607,882 B1 | 8/2003 | Cox et al. | |
| 6,689,558 B2 | 2/2004 | Case | |
| 6,824,978 B1 | 11/2004 | Cox et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,163,824 B2 | 1/2007 | Cox et al. | |
| 7,914,796 B2 | 3/2011 | Miller et al. | |
| 8,034,598 B2 | 10/2011 | Miller | |
| 8,623,618 B2 * | 1/2014 | Doyon .................... | C12N 15/52 |
| | | | 435/325 |
| 8,962,281 B2 * | 2/2015 | Doyon .................. | C12N 15/907 |
| | | | 435/320.1 |
| 9,150,879 B2 * | 10/2015 | Doyon .................... | C12N 15/52 |
| 9,376,689 B2 * | 6/2016 | Doyon .................... | C07K 14/47 |
| 9,765,361 B2 * | 9/2017 | Doyon ..................... | C12N 9/10 |
| 10,066,242 B2 * | 9/2018 | Doyon .................... | C12N 15/85 |
| 10,640,790 B2 * | 5/2020 | Doyon ...................... | C07K 7/06 |
| 11,136,599 B2 * | 10/2021 | Doyon ...................... | C12N 9/22 |

(Continued)

FOREIGN PATENT DOCUMENTS

| | | |
|---|---|---|
| WO | WO 1995/19431 A1 | 7/1995 |
| WO | WO 1996/06166 A1 | 2/1996 |

(Continued)

OTHER PUBLICATIONS

Boch, et al., "Breaking the Code of DNA Binding Specificity of TAL-Type III Effectors," *Science* 326:1509-1512 (2009).

Chica, et al., "Semi-Rational Approaches To Engineering Enzyme Activity: Combining the Benefits of Directed Evolution and Rational Design," *Current Opinion in Biotechnology* 16(4):378-384 (2005).

Guo, et al., "Directed Evolution of an Enhanced and Highly Efficient FokI Cleavage Domain for Zinc Finger Nucleases," *J. Mol. Biol.* 400:96-107 (2010).

Miller, et al., "An Improved Zinc-Finger Nuclease Architecture for Highly Specific Genome Editing," *Nat Biotechnology* 25:778-785 (2007).

(Continued)

*Primary Examiner* — Christian L Fronda
(74) *Attorney, Agent, or Firm* — Foley & Lardner LLP

(57) ABSTRACT

Disclosed herein are engineered cleavage half-domains; fusion polypeptides comprising these engineered cleavage half-domains; polynucleotides encoding the engineered cleavage half-domains and fusion proteins; and cells comprising said polynucleotides and/or fusion proteins. Also described are methods of using these polypeptides and polynucleotides, for example for targeted cleavage of a genomic sequence.

18 Claims, 26 Drawing Sheets

Specification includes a Sequence Listing.

(56) References Cited

U.S. PATENT DOCUMENTS

| | | |
|---|---|---|
| 2003/0108880 A1 | 6/2003 | Rebar et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0063231 A1 | 3/2006 | Li et al. |
| 2006/0188987 A1 | 8/2006 | Guschan et al. |
| 2008/0131962 A1 | 6/2008 | Miller |
| 2008/0131963 A1 | 6/2008 | Doucette-Stamm et al. |
| 2008/0159996 A1 | 7/2008 | Ando et al. |
| 2008/0188000 A1 | 8/2008 | Reik et al. |
| 2009/0029468 A1 | 1/2009 | Barbas, III et al. |
| 2009/0111119 A1 | 4/2009 | Doyon et al. |
| 2009/0305346 A1 | 12/2009 | Miller |
| 2010/0291048 A1 | 11/2010 | Holmes et al. |

FOREIGN PATENT DOCUMENTS

| | | |
|---|---|---|
| WO | WO 1998/53057 A1 | 11/1998 |
| WO | WO 1998/53058 A1 | 11/1998 |
| WO | WO 1998/53059 A1 | 11/1998 |
| WO | WO 1998/53060 A1 | 11/1998 |
| WO | WO 1998/54311 A1 | 12/1998 |
| WO | WO 1900/27878 A1 | 5/2000 |
| WO | WO 2001/60970 A2 | 8/2001 |
| WO | WO 2001/88197 A2 | 11/2001 |
| WO | WO 2002/016536 A1 | 2/2002 |
| WO | WO 2002/099084 A2 | 12/2002 |
| WO | WO 2003/016496 A2 | 2/2003 |
| WO | WO 2005/014791 A2 | 2/2005 |
| WO | WO 2007/014275 A2 | 1/2007 |
| WO | WO 2007/139898 A2 | 12/2007 |

OTHER PUBLICATIONS

Miller, et al., "A Tale Nuclease Architecture for Efficient Genome Editing," *Nature Biotechnology* 29:143-148 (2011).

Moscou, et al., "A Simple Cipher Governs DNA Recognition by TAL Effectors," *Science* 326:1501 (2009).

Perez, et al., "Establishment of HIV-1 Resistance in CD4+ T Cells by Genome Editing Using Zinc-Finger Nucleases," *Nature Biotechnology* 26:808-816(2008).

Sen, et al., "Developments in Directed Evolution for Improving Enzyme Functions," *Appl. Biochem. Biotechnol.* 14(3):212-223 (2007).

Singh, et al., "Protein Engineering Approaches in the Post-Genomic Era," *Current Protein and Peptide Science* 18:1-11 (2017).

Szczpek, et al., "Structure-Based Redesign of the Dimerization Interface Reduces the Toxicity of Zinc-Finger Nucleases," *Nat. Biotechnol.* 25:786-793 (2007).

Urnov, et al., "Highly Efficient Endogenous Human Gene Correction Using Designed Zinc-Finger Nucleases," *Nature* 435:646-651 (2005).

Wah, et al., "Structure of Foki Has Implications for DNA Cleavage," *PNAS USA* 95:10564-10569 (1998).

Yoshikuni, et al., "Pathway Engineering by Designed Divergent Evolution," *Curr Opin Chem Biol* 11(2):233-9 (2007).

\* cited by examiner

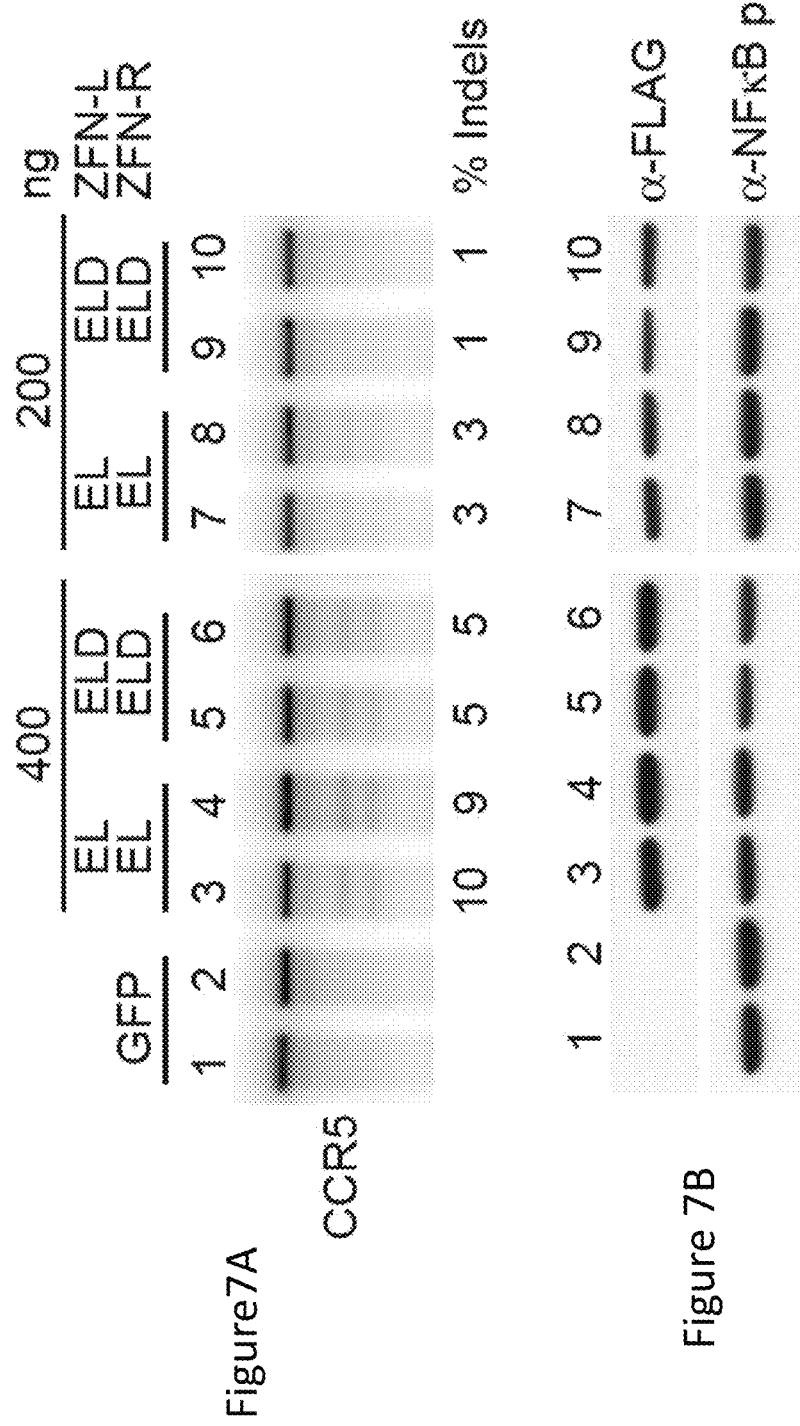

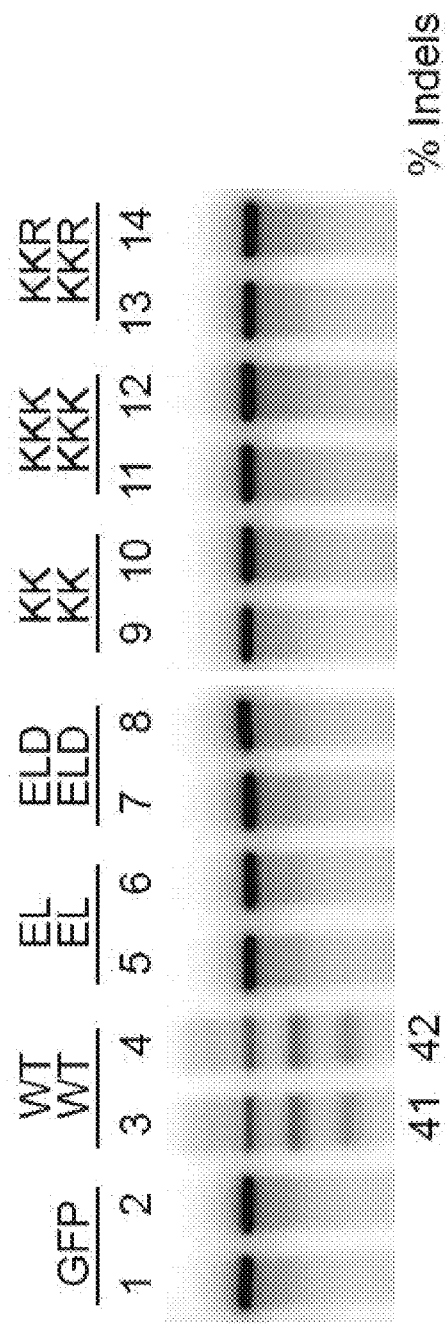
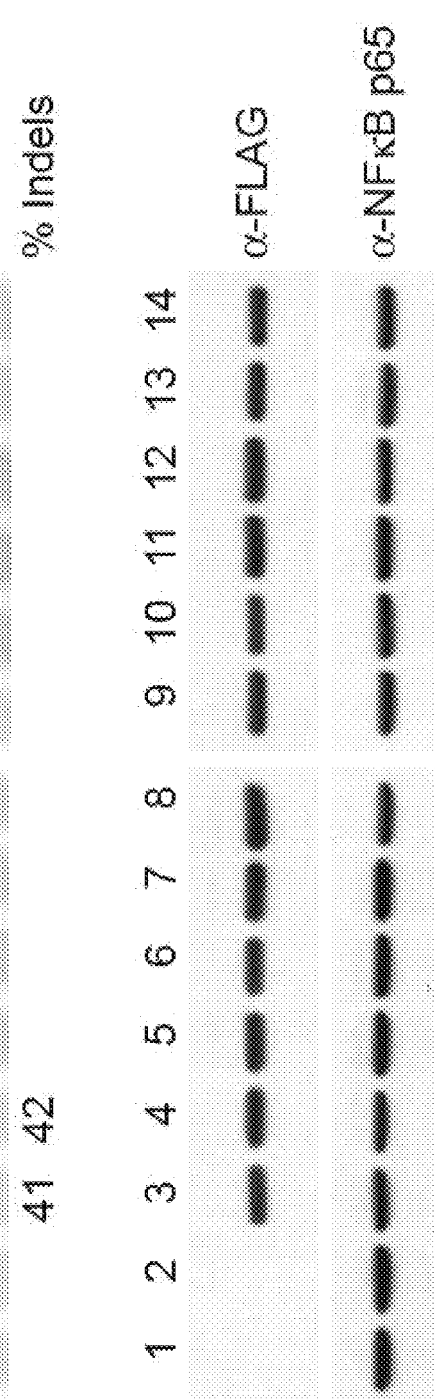
Fig 8a
Fig 8b

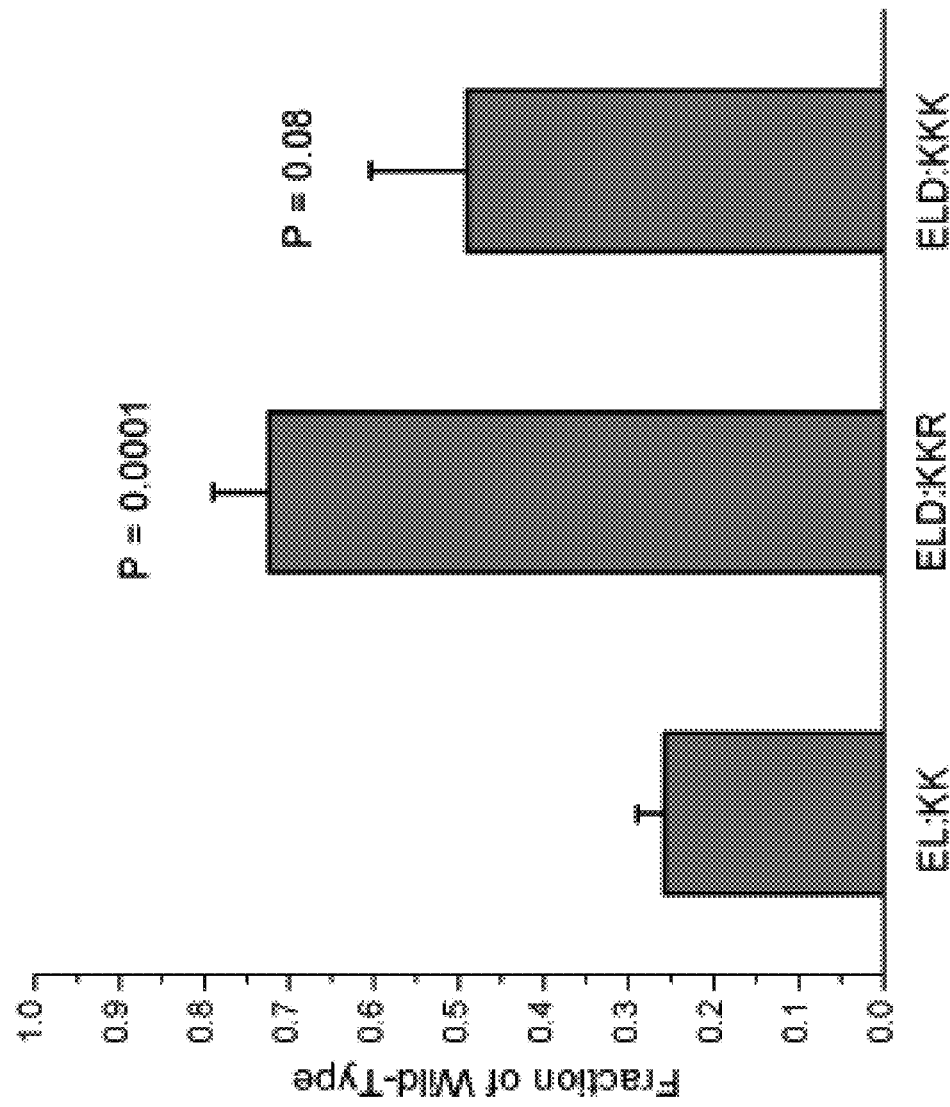

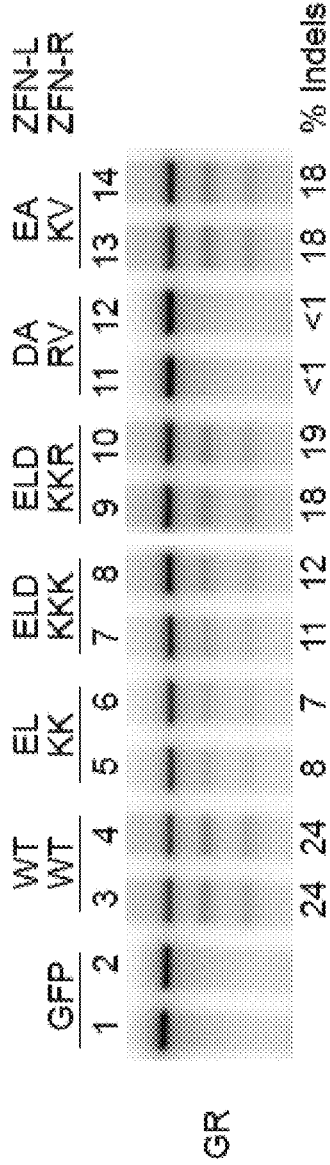
Figure 12A- GR
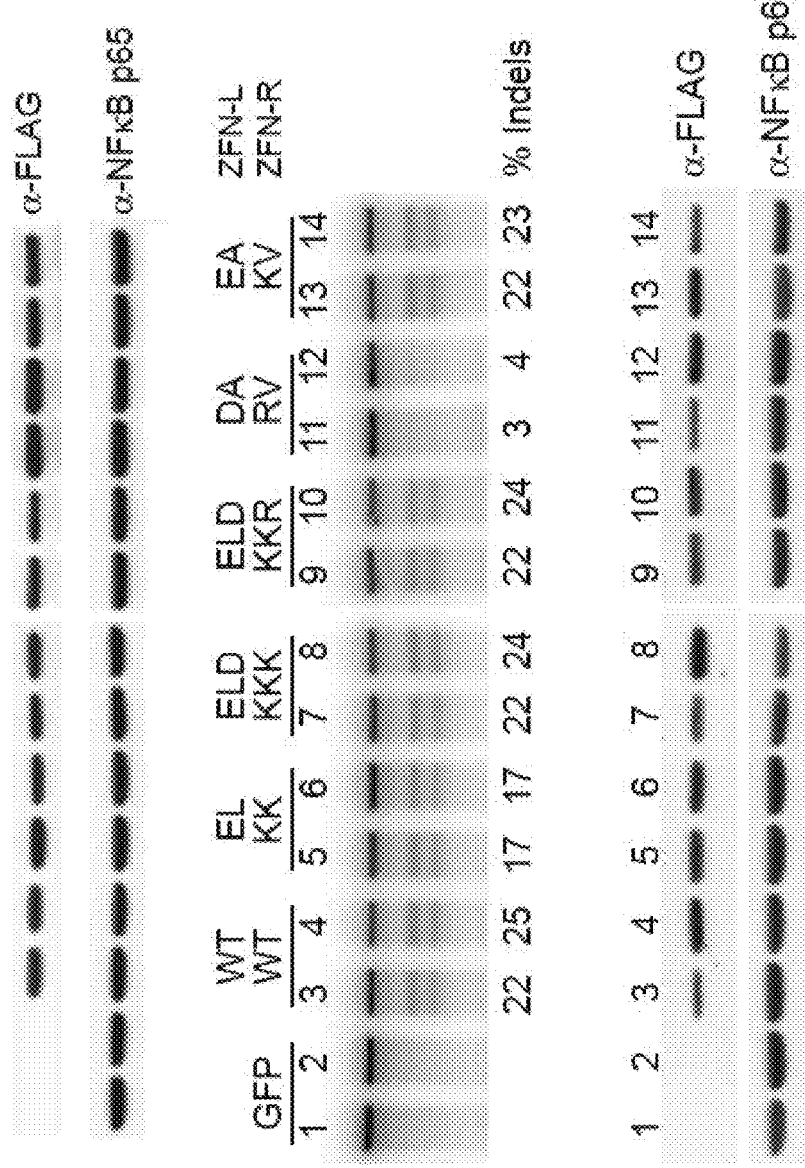
Figure 12B- CCR5

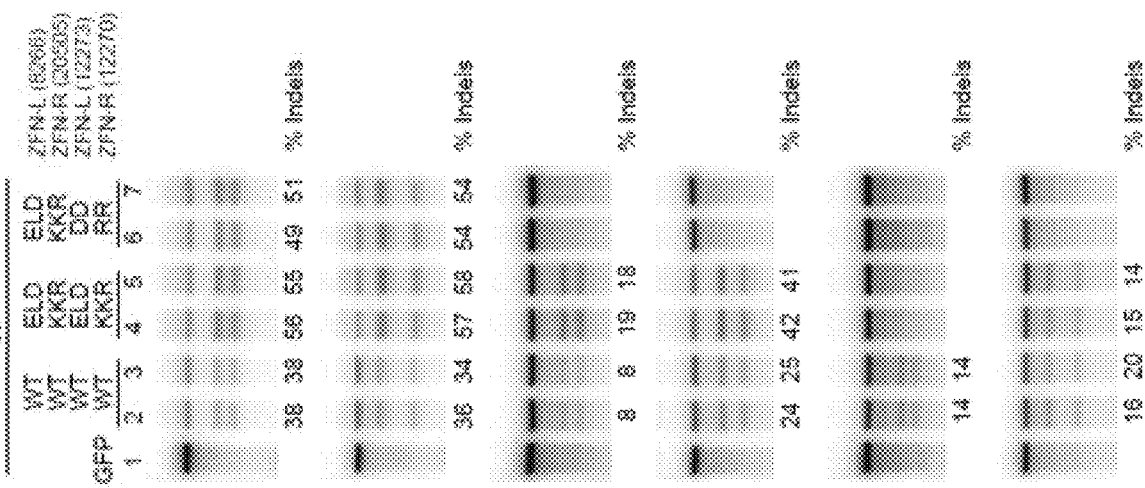
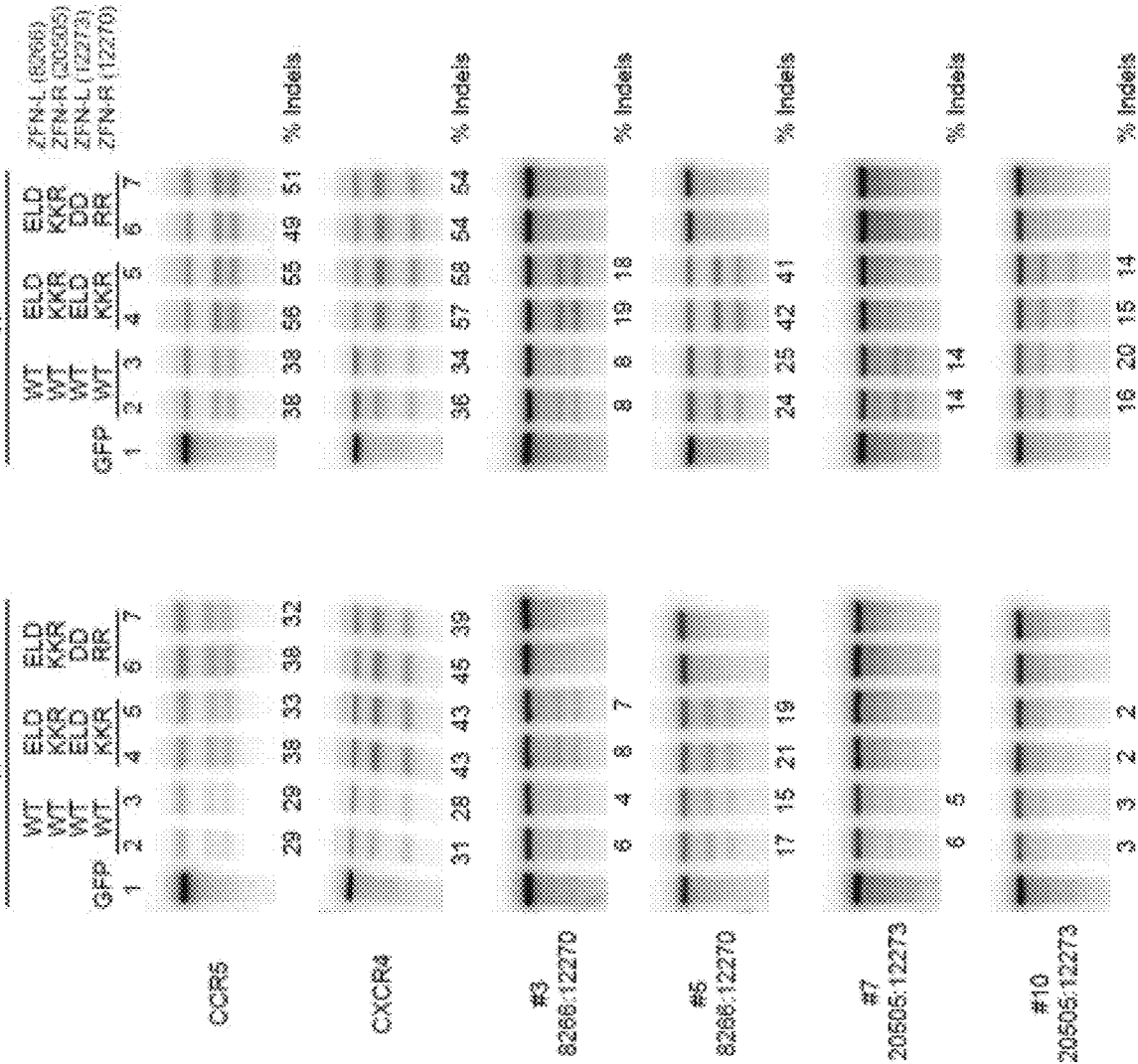

ARTIFICIAL NUCLEASES COMPRISING ENGINEERED CLEAVAGE HALF-DOMAINS

CROSS-REFERENCE TO RELATED APPLICATIONS

The present application is a continuation of U.S. patent application Ser. No. 16/838,804, filed Apr. 2, 2020, now U.S. Pat. No. 11,136,599 which is a continuation of U.S. patent application Ser. No. 16/055,525, filed Aug. 6, 2018, now U.S. Pat. No. 10,640,790, which is a continuation of U.S. patent application Ser. No. 15/660,072, filed Jul. 26, 2017, now U.S. Pat. No. 10,066,242, which is a continuation of U.S. patent application Ser. No. 15/160,571, filed May 20, 2016, now U.S. Pat. No. 9,765,361, which is a continuation of U.S. patent application Ser. No. 14/627,812, filed Feb. 20, 2015, now U.S. Pat. No. 9,376,689, which is a continuation of U.S. patent application Ser. No. 12/931,660, filed Feb. 7, 2011, now U.S. Pat. No. 8,962,281, which claims the benefit of U.S. Provisional Application Nos. 61/337,769, filed Feb. 8, 2010 and 61/403,916, filed Sep. 23, 2010, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Oct. 4, 2021, is named 128687-2783_SL.txt and is 18,785 bytes in size.

STATEMENT OF RIGHTS TO INVENTIONS MADE UNDER FEDERALLY SPONSORED RESEARCH

Not applicable.

TECHNICAL FIELD

The present disclosure is in the fields of polypeptide and genome engineering and homologous recombination.

BACKGROUND

Artificial nucleases, such as zinc finger nucleases (fusions of zinc finger domains and cleavage domains) for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, U.S. Patent Publication Nos. 2003/0232410; 2005/0208489; 2005/0026157; 2005/0064474; 2006/0188987; 2006/0063231; and International Publication No. WO 07/014275, the disclosures of which are incorporated by reference in their entireties for all purposes.

To increase specificity, a pair of fusion proteins, each comprising a zinc finger binding domain and cleavage half-domain can be used to cleave the target genomic DNA. Because cleavage does not occur unless the cleavage half-domains associate to form a functional dimer, this arrangement increases specificity.

To further decrease off-target cleavage events, engineered cleavage half-domains, for example domains that form obligate heterodimers, have also been developed. See, e.g., U.S. Patent Publication No. 2008/0131963. However, there remains a need for additional engineered cleavage half-domains with increased activity and decreased off-target cleavage activity.

SUMMARY

The present disclosure provides engineered cleavage half-domains that exhibit enhanced activity and specificity as compared to wild-type cleavage domains and/or previously described engineered cleavage half-domains. Also described are complexes (e.g., heterodimers) and fusion proteins comprising these engineered cleavage half-domains. The disclosure also provides methods of using these compositions for targeted cleavage of cellular chromatin in a region of interest and/or homologous recombination at a predetermined region of interest in cells.

Thus, in one aspect, described herein is an engineered cleavage half-domain comprising two or more mutations as compared to the parental wild-type cleavage domain from which they are derived. In certain embodiments, the engineered cleavage half-domains are derived from FokI and comprise a mutation in two or more of amino acid residues 418, 432, 441, 481, 483, 486, 487, 490, 496, 499, 523, 527, 537, 538 and/or 559, numbered relative to a wild-type FokI cleavage half-domain. In one embodiment, the engineered cleavage half-domain is derived from a wild-type FokI cleavage domain and comprises mutations in amino acid residues 486, 499 and 496, numbered relative to wild-type FokI. In another embodiment, the engineered cleavage half-domain comprises mutations in amino acid residues 490, 538 and 537, numbered relative to wild-type FokI. In another embodiment, the engineered cleavage half domains are derived from a wild-type FokI cleavage domain and comprise mutations in the amino acid residues 487, 499 and 496, numbered relative to wild-type FokI. In one embodiment, the engineered cleavage half domains are derived from a wild-type FokI cleavage domain and comprise mutations in the amino acid residues 483, 538 and 537, numbered relative to wild-type FokI. In still further embodiments, the engineered cleavage half-domain comprises mutations in the amino acid residues 490 and 537.

The engineered cleavage half-domains described herein can form heterodimers with wild-type cleavage half-domains and/or with other engineered cleavage half-domains. In certain embodiments, the engineered cleavage half-domain comprises mutations at positions 486, 499 and 496 (numbered relative to wild-type FokI), for instance mutations that replace the wild-type Gln (Q) residue at position 486 with a Glu (E) residue, the wild-type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild-type Glu (E) residue at position 490 with a Lys (K) residue, the wild-type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild-type Glu (E) residue at position 490 with a Lys (K) residue and the wild-type His (H) residue at position 537 with a Lys (K) residue or a Arg (R) residue (also referred to as "KIK" and "KIR" domains, respectively). In still further embodiments, the engineered cleavage half-domain comprises mutations at positions 487 and 496 (numbered relative to wild-type FokI), for instance mutations that replace the wild-type Arg (R) residue at position 487 with an Asp (D) residue and the wild-type Asn (N) residue at position 496 with an Asp (D) residue (also referred to as "DD") and/or mutations at positions 483 and 537 (numbered relative to wild-type FokI), for instance, mutations that replace the wild-type Asp (D) residue at position 483 with an Arg (R) residue and the wild-type His (H) residue at position 537 with an Arg (R) residue (also referred to as "RR"). In other embodiments, the engineered cleavage half-domain comprises mutations at positions 487, 499 and 496 (numbered relative to wild-type FokI), for instance mutations that replace the wild-type Arg (R) residue at position 487 with an Asp (D) residue and the wild-type Ile (I) residue at position 499 with an Ala (A) and the wild-type Asn (N) residue at position 496 with an Asp (D) residue (also referred to as "DAD") and/or mutations at positions 483, 538 and 537 (numbered relative to wild-type FokI), for instance, mutations that replace the wild-type Asp (D) residue at position 483 with an Arg (R) residue and the wild-type Ile (I) residue at position 538 with a Val (V) residue, and the wild-type His (H) residue at position 537 with an Arg (R) residue (also referred to as "RVR").

In another aspect, the engineered cleavage half domains may be further engineered to contain mutations in domain of the FokI other than the dimerization domain. For example, mutations at positions 418, 432, 441, 481, 523, 527 and 559 have been shown to increase the catalytic activity of a wild-type FokI domain. In particular, the mutations where Pro (P) replaces the wild-type Ser (S) residue at position 418 and where a Glu (E) residue replaces the wild-type Lys (K) residue at position 441 (known as "PE", also known as "Sharkey") have been shown to enhance catalytic activity (see Guo, et al., (2010) *J Mol Biol*, doi:10.101b/j.jmb.2010.04.060). In another aspect, the mutations where Pro (P) replaces the wild-type Ser (S) at position 418, where Leu (L) replaces the wild-type Phe (F) at position 432, where Glu (E) replaces the wild-type Lys (K) at position 441, where His (H) replaces the wild-type Gln (Q) at position 481, where Tyr (Y) replaces the wild-type His (H) at position 523, where Asp (D) replaces the wild-type Asn (N) at position 527 and Gln (Q) replaces the wild-type Lys (K) at position 559 (known as "Sharkey", see Guo, et al., ibid). Thus in one embodiment, the mutant FokI domain may comprise mutations at positions 418, 441, 486, and 499. In another embodiment, the mutant FokI domain may comprise mutations at positions 418, 441, 490, and 538. In further embodiments, the wild-type FokI domain may be mutated to include mutations at positions 418, 441, 486, 496 and 499, and/or 418, 441, 490, 537, and 538. In other embodiments, the wild-type FokI domain may be mutated at positions 418, 432, 441, 481, 486, 496, 499 523, 527 and 559 and/or positions 418, 432, 441, 481, 523, 527, 559, 490, 538 and 537. In particular, the mutations may include mutation of the wild-type Gln (Q) at position 486 with Glu (E), mutation of the wild-type Ile (I) at position 499 with a Leu (L), mutation of the wild-type Asn (N) at position 496 with an Asp (D), mutation of the wild-type Ser (S) at position 418 with a Pro (P) and mutation of the wild-type Lys (K) at position 441 with a Glu (E) (also known as "ELD-S" or "ELD Sharkey") and/or mutation of the wild-type Glu (E) at position 490 with a Lys (K), mutation of the wild-type Ile (I) at position 538 with a Lys (K), mutation of the wild-type His (H) at position 537 with an Lys (K) or Arg(R), mutation of the wild-type Ser (S) at position 418 with a Pro (P) and mutation of the wild-type Lys (K) at position 441 with a Glu (E) residue (also known as KKK-S or KKR-S, or KKK-Sharkey or KKR-Sharkey). Further embodiments encompass S418P: F432L:K441E:Q481H:Q486E:N496D:I499L: H523Y: N527D:K559Q, also known as ELD-Sharkey', and S418P: F432L:K441E:Q481H:E490K:H523Y:N527D:H537K or R:I538K:K559Q, also known as KKK-Sharkey' or KKR-Sharkey'.

In another aspect, engineered cleavage half domains that display conditional activity (for example, depending on conditions under which the cells are maintained) are provided. In some embodiments, the conditional engineered cleavage half domains display a decrease in activity under decreased temperature conditions. In some embodiments, the conditional engineered cleavage half domains display a decrease in activity under increased temperature conditions.

In yet another aspect, engineered cleavage half domains may be incorporated into zinc finger nucleases comprising non-canonical zinc-coordinating residues (e.g. CCHC rather than the canonical C2H2 configuration, see U.S. Patent Publication No. 2003/0108880).

In another aspect, fusion polypeptides comprising a DNA binding domain and an engineered cleavage half-domain as described herein are provided. In certain embodiments, the DNA-binding domain is a zinc finger binding domain (e.g., an engineered zinc finger binding domain). In other embodiments, the DNA-binding domain is a TALE DNA-binding domain.

In another aspect, polynucleotides encoding any of the engineered cleavage half-domains or fusion proteins as described herein are provided.

In yet another aspect, cells comprising any of the polypeptides (e.g., fusion polypeptides) and/or polynucleotides as described herein are also provided. In one embodiment, the cells comprise a pair of fusion polypeptides, one fusion polypeptide comprising an ELD or ELE cleavage half-domain and one fusion polypeptide comprising a KKK or KKR cleavage half-domain. In another embodiment, one fusion polypeptide comprises a DAD cleavage half domain while another comprises the RVR fusion polypeptide. In other embodiments, the paired fusion polypeptides further comprise mutations in other locations of the FokI nuclease domain. In some embodiments, these catalytic domain mutants are S418P and K441E, thus these mutant fusion polypeptides comprise the mutant FokI domains listed below:
  (a) EL-S: S418P:K441E:Q486E:I499L
  (b) KK-S: S418P:K441E:E490K:I538K
  (c) ELD-S: S418P:K441E:Q486E:N496D:I499L
  (d) KKK-S: S418P:K441E:E490K:H537K:I538K
  (e) KKR-S: S418P:K441E:E490K:H537R:I538K
  (f) DA-S: S418P:K441E:R487D:I499A
  (g) RV-S: S418P:K441E:D483R:I538V
  (h) DAD-S: S418P:K441E:R487D:N496D:I499A
  (i) RVR-S: S418P:K441E:D483R:H537R:I538V
  (j) DD-S: S418P:K441E:R487D:N496D
  (k) RR-S: S418P:K441E:D483R:H537R.

In yet another aspect, methods for targeted cleavage of cellular chromatin in a region of interest; methods of causing homologous recombination to occur in a cell; methods of treating infection; and/or methods of treating disease are provided. The methods involve cleaving cellular chromatin at a predetermined region of interest in cells by expressing a pair of fusion polypeptides as described herein (i.e., a pair of fusion polypeptides in which one fusion polypeptide comprises the engineered cleavage half-domains as described herein).

The engineered cleavage half domains described herein can be used in methods for targeted cleavage of cellular chromatin in a region of interest and/or homologous recombination at a predetermined region of interest in cells. Cells include cultured cells, cells in an organism and cells that have been removed from an organism for treatment in cases where the cells and/or their descendants will be returned to the organism after treatment. A region of interest in cellular chromatin can be, for example, a genomic sequence or portion thereof. Compositions include fusion polypeptides comprising a DNA binding domain (e.g., an engineered zinc finger binding domain or TALE binding domain having a novel specificity) and a cleavage half domain as described.

A fusion protein can be expressed in a cell, e.g., by delivering the fusion protein to the cell or by delivering a polynucleotide encoding the fusion protein to a cell, wherein the polynucleotide, if DNA, is transcribed, and an RNA molecule delivered to the cell or a transcript of a DNA molecule delivered to the cell is translated, to generate the fusion protein. Methods for polynucleotide and polypeptide delivery to cells are presented elsewhere in this disclosure.

Accordingly, in another aspect, a method for cleaving cellular chromatin in a region of interest can comprise (a) selecting a first sequence in the region of interest; (b) engineering a first DNA binding domain (e.g., zinc finger or TALE DNA binding domain) to bind to the first sequence; (c) expressing a first fusion protein in the cell, the first fusion protein comprising the first DNA-binding domain and a first engineered cleavage half-domain as described herein; and (d) expressing a second fusion protein in the cell, the second fusion protein comprising a second DNA binding domain and a second cleavage half-domain as described herein, wherein the first fusion protein binds to the first sequence, and the second fusion protein binds to a second sequence located between 2 and 50 nucleotides from the first sequence, thereby positioning the engineered cleavage half-domains such that they form a heterodimer, which heterodimer cleaves cellular chromatin in the region of interest.

In other embodiments, any of the methods described herein may comprise (a) selecting first and second sequences in a region of interest, wherein the first and second sequences are between 2 and 50 nucleotides apart; (b) engineering a first DNA binding domain (e.g., zinc finger or TALE DNA binding domain) to bind to the first sequence; (c) engineering a second zinc finger binding domain to bind to the second sequence; (d) expressing a first fusion protein in the cell, the first fusion protein comprising the first DNA-binding domain and a first cleavage half-domain as described herein; (e) expressing a second fusion protein in the cell, the second fusion protein comprising the second DNA binding domain (e.g., engineered zinc finger or TALE DNA binding domain) and a second cleavage half-domain as described herein; wherein the first fusion protein binds to the first sequence and the second fusion protein binds to the second sequence, thereby positioning the first and second engineered cleavage half-domains such that they form a heterodimer which cleaves the cellular chromatin in the region of interest. In certain embodiments, cellular chromatin is cleaved at one or more sites between the first and second sequences to which the fusion proteins bind.

In further embodiments, a method for cleavage of cellular chromatin in a region of interest comprises (a) selecting the region of interest; (b) engineering a first DNA binding domain (e.g., zinc finger or TALE DNA binding domain) to bind to a first sequence in the region of interest; (c) providing a second DNA binding domain (e.g., zinc finger or TALE DNA binding domain) which binds to a second sequence in the region of interest, wherein the second sequence is located between 2 and 50 nucleotides from the first sequence; (d) expressing a first fusion protein in the cell, the first fusion protein comprising the first DNA binding domain and a first cleavage half-domain as described herein; and (e) expressing a second fusion protein in the cell, the second fusion protein comprising the second DNA binding domain and a second cleavage half domain as described herein; wherein the first fusion protein binds to the first sequence, and the second fusion protein binds to the second sequence, thereby positioning the first and second cleavage half-domains such that they form a heterodimer and the cellular chromatin is cleaved in the region of interest.

Also provided are methods of altering a region of cellular chromatin, for example to introduce targeted mutations. In certain embodiments, methods of altering cellular chromatin comprise introducing into the cell one or more targeted nucleases to create a double-stranded break in cellular chromatin at a predetermined site, and a donor polynucleotide, having homology to the nucleotide sequence of the cellular chromatin in the region of the break. Cellular DNA repair processes are activated by the presence of the double-stranded break and the donor polynucleotide is used as a template for repair of the break, resulting in the introduction of all or part of the nucleotide sequence of the donor into the cellular chromatin. Thus, a sequence in cellular chromatin can be altered and, in certain embodiments, can be converted into a sequence present in a donor polynucleotide.

Targeted alterations include, but are not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations.

The donor polynucleotide can be DNA or RNA, can be linear or circular, and can be single-stranded or double-stranded. It can be delivered to the cell as naked nucleic acid, as a complex with one or more delivery agents (e.g., liposomes, poloxamers) or contained in a viral delivery vehicle, such as, for example, an adenovirus or an adeno-associated Virus (AAV). Donor sequences can range in length from 10 to 1,000 nucleotides (or any integral value of nucleotides therebetween) or longer.

In certain embodiments, the frequency of homologous recombination can be enhanced by arresting the cells in the G2 phase of the cell cycle and/or by activating the expression of one or more molecules (protein, RNA) involved in homologous recombination and/or by inhibiting the expression or activity of proteins involved in non-homologous end-joining.

In any of the methods described herein, the second zinc finger binding domain may be engineered to bind to the second sequence.

Furthermore, in any of the methods described herein, the fusion proteins may be encoded by a single polynucleotide.

For any of the aforementioned methods, the cellular chromatin can be in a chromosome, episome or organellar genome. Cellular chromatin can be present in any type of cell including, but not limited to, prokaryotic and eukaryotic cells, fungal cells, plant cells, animal cells, mammalian cells, primate cells and human cells.

In some aspects, the methods provide for organisms comprising fusion proteins with conditional FokI activity comprising the mutations described herein. In some embodiments, these organisms are plants. These methods also relate to the tissues of such plants including seeds.

In other embodiments, a method for cleavage of cellular chromatin in two or more regions of interest is provided. The method comprises (a) selecting the first region of interest; (b) engineering a first DNA binding domain (e.g., zinc finger or TALE DNA binding domain) to bind to a first sequence in the first region of interest; (c) providing or engineering a second DNA binding domain (e.g., zinc finger or TALE DNA binding domain) which binds to a second sequence in the first region of interest, wherein the second sequence is located between 2 and 50 nucleotides from the first sequence; (d) selecting the second region of interest; (e) providing or engineering a third DNA binding domain (e.g., zinc finger or TALE DNA binding domain) to bind to a first sequence in the second region of interest; (f) providing or engineering a fourth DNA binding domain (e.g., zinc finger or TALE DNA binding domain) which binds to a second sequence in the second region of interest, wherein the second sequence is located between 2 and 50 nucleotides from the first sequence; (g) expressing a first fusion protein in the cell, the first fusion protein comprising the first DNA binding domain and a first cleavage half-domain as described herein; and (h) expressing a second fusion protein in the cell, the second fusion protein comprising the second DNA binding domain and a second cleavage half domain as described herein; wherein the first fusion protein binds to the first sequence, and the second fusion protein binds to the second sequence, thereby positioning the first and second cleavage half-domains such that they form a heterodimer and the cellular chromatin is cleaved in the first region of interest, (i) expression a third fusion protein in the cell, the third fusion protein comprising the third DNA binding domain and a third cleavage half domain as described herein, and (j) expressing a fourth fusion protein in the cell, the fourth protein comprising the fourth DNA binding domain and a fourth cleavage half domain as described herein; wherein the third fusion protein binds to the first sequence in the second region of interest, and the fourth fusion protein binds to the second sequence in the second region of interest, thereby position the third and fourth cleavage half domains such that they form a heterodimer and the cellular chromatin in cleaved in the second region of interest.

In addition, in any of the methods described herein, at least one zinc finger binding domain is engineered, for example by design or selection methods.

BRIEF DESCRIPTION OF THE DRAWINGS

FIG. 1A shows the results when a yeast reporter strain was transformed with the isolated mutant vectors, divided into three cultures, and incubated at 22° C., 30° C., and 37° C. Following ZFN induction, the activity of the mutants was determined and reported as a fraction of the wild-type ZFN. FIG. 1B shows mutant ZFN expression as monitored by western blot using the anti-FLAG antibody. To verify equal protein loading an anti-Histone 3 (anti-H3) antibody western blot was performed.

FIG. 2A depicts the activity of the 53BP1-specific ZFN variant constructs that were nucleofected in K562 cells. The cells were harvested 3 days post-transfection. Two cultures of each combination were assayed (e.g. EL/KK 5 and 6). The Cel-1 assay (Surveyor™, Transgenomic) was used to determine the frequency of ZFN-induced insertions and deletions (% indels), shown in FIG. 2A at the bottom of each lane. ZFN-induced indels are a consequence of a double strand break (DSB) as a result of ZFN cleavage of the DNA, which is then followed by repair by the cell using the Non-Homologous End Joining (NHEJ) process, which can insert or delete small portions of DNA at the break site during repair. Arrows indicate expected sizes of bands following Cel-1 cleavage. An aliquot of the cells was also cultivated for an additional week to determine the stability of the modified cells in extended cultures (Day 10). FIG. 2B depicts ZFN expression as monitored by western blot using the anti-FLAG antibody. As a loading control, anti-NFκB p65 was used.

FIG. 3A depicts Cel-1 activity assays results of KDR-specific ZFN pairs in K562 cells, monitored at 3 and 20-days post nucleofection. The ZFN pair with indicated FokI mutants used in each lane is shown above the lane and the activity as detected by the Cel-I assay (as described above for FIG. 2) is shown at the bottom. GFP indicates a negative control. ZFN FokI variants ELD:KKK and ELD:KKR are more active than the original obligate heterodimeric ZFN (EL:KK). FIG. 3B depicts monitoring of ZFN expression and protein loading as described above for FIG. 1.

FIG. 5A depicts Cel-1 activity assays (as described above for FIG. 2) for two different ZFN pairs targeting the RIPK1 gene (A and B) that were nucleofected in K562 cells. Cells were harvested 3 days post-transfection, and the assays were used to determine the frequency of ZFN-induced insertions and deletions (indels). The percent indels are shown at the bottom of each lane. FIG. 5B shows the results when K562 cells were nucleofected with a third pair of ZFN expression vectors (C) targeting the RIPK1 gene and incubated for 3 days at 37° C. (left panel) or 30° C. (right panel).

FIG. 6A shows the activity of forced homodimerization of CCR5 targeting ZFNs after nucleofection of indicated FokI variants in K562 cells using the Cel-1 assay to determine the frequency of ZFN-induced indels at the CCR5 heterodimer target, a CCR5-L ZFN homodimer (ABLIM2), and a CCR5-R homodimer (PGC) off-target sites. FIG. 6B depicts monitoring of ZFN expression and protein loading as described above for FIG. 1.

FIGS. 7A and 7B shows Cel-1 activity assays results (as described above for FIG. 2) of the CCR5 variants described in FIG. 6. FIG. 7A depicts the Cel-1 activity results using decreasing amounts of CCR5 EL and ELD FokI variants. These constructs were nucleofected in K562 and the Cel-1 assay was used to determine the frequency of ZFN-induced indels at the CCR5 heterodimer site. FIG. 7B depicts monitoring of ZFN expression and protein loading as described above for FIG. 1.

FIGS. 8A and 8B show Cel-1 activity assay results of forced homodimerization of mutants in the GR-specific ZFN background. FIG. 8A depicts the Cel-1 results after forced homodimerization of GR targeting ZFNs after nucleofection of indicated FokI variants in K562 cells to determine the frequency of ZFN-induced indels at the GR heterodimer site. No indels were detectable in this assay in samples other that wild-type. FIG. 8B depicts monitoring of ZFN expression and protein loading as described above for FIG. 1.

FIG. 10A shows the Cel-1 activity assay results (as described above for FIG. 2) using decreasing amounts of CCR5-targeting ZFNs that were nucleofected in PBMCs. The cells were harvested 3 days post-transfection, and the Cel-1 assay was used to determine the frequency of ZFN-induced indels. FIG. 10B depicts the results in a bar graph with three different ZFN pairs (ZFN A, ZFN B, and ZFN C, see Example 5) targeting the PD1 gene that were nucleofected in duplicate in PBMCs. The cells were harvested 3 and 10 days post-transfection, and the Cel-1 assay was used to determine the frequency of ZFN-induced indels. The graph shows the mean values and error bars from the duplicate transfections.

FIGS. 11A through 11C depict the activity of the novel ZFN mutants. FIG. 11A shows the Cel-1 activity assay results using decreasing amounts of GR-targeting ZFNs that were nucleofected in PBMCs. The cells were harvested 3 and 10 days post-transfection, and the Cel-1 assay was used to determine the frequency of ZFN-induced indels. FIG. 11B depicts a bar graph showing the mean values+/− s.e.m. (standard error of the mean) of the relative activities of the indicated ZFNs from six independent transfections in PBMCs. P-values use the two-sample T-test calculated by MicroCal Origins version 7.5 (OriginLab®), showing the significance of the indicated activities with respect to the EL-KK variant. FIG. 11C depicts the use of the EL/KK and ELD/KKR GR-specific ZFN pairs nucleofected in K562 cells for promoting targeted integration of a donor nucleic acid. The donor in this experiment comprised a novel BamHI restriction site so that upon targeted integration of the DNA, a PCR amplification product of the targeted area would be able to be cut by the BamHI restriction enzyme if TI had occurred. The data show that the ELD/KKR FokI mutant pair was more efficient at promoting TI than the EL/KK FokI mutant pair.

FIGS. 12A and 12B depict the activity of FokI mutants specific for either GR or CCR5. FIG. 12A shows the Cel-I activity assay (as described above for FIG. 2) results using FokI mutants of GR-targeting ZFNs that were nucleofected in K562 cells. See Table 4 for a specific description of the locations of the mutated amino acids. FIG. 12B shows similar results for CCR5 targeting ZFNs. The results demonstrate that the DA/RV pair is the least active of all FokI mutant pairs tested.

FIG. 19A shows the additive results of the FokI mutants, and FIG. 19B shows the results of monitoring expression and gel loading as described for Example 1.

FIGS. 20A and 20C show the additive results of the FokI mutants, and FIGS. 20B and 20D show the results of monitoring expression and gel loading as described for Example 1.

FIG. 21B shows results of monitoring expression and gel loading as described for Example 1.

FIGS. 22A and 22B depict activity results of the various FokI mutants in the context of the indicated ZFNs at 37° C.

(FIG. 22A) or 30° C. (FIG. 22B) as assayed by Cel-I assay. The percentage of indels is indicated below the lanes.

DETAILED DESCRIPTION

Figure 1A:
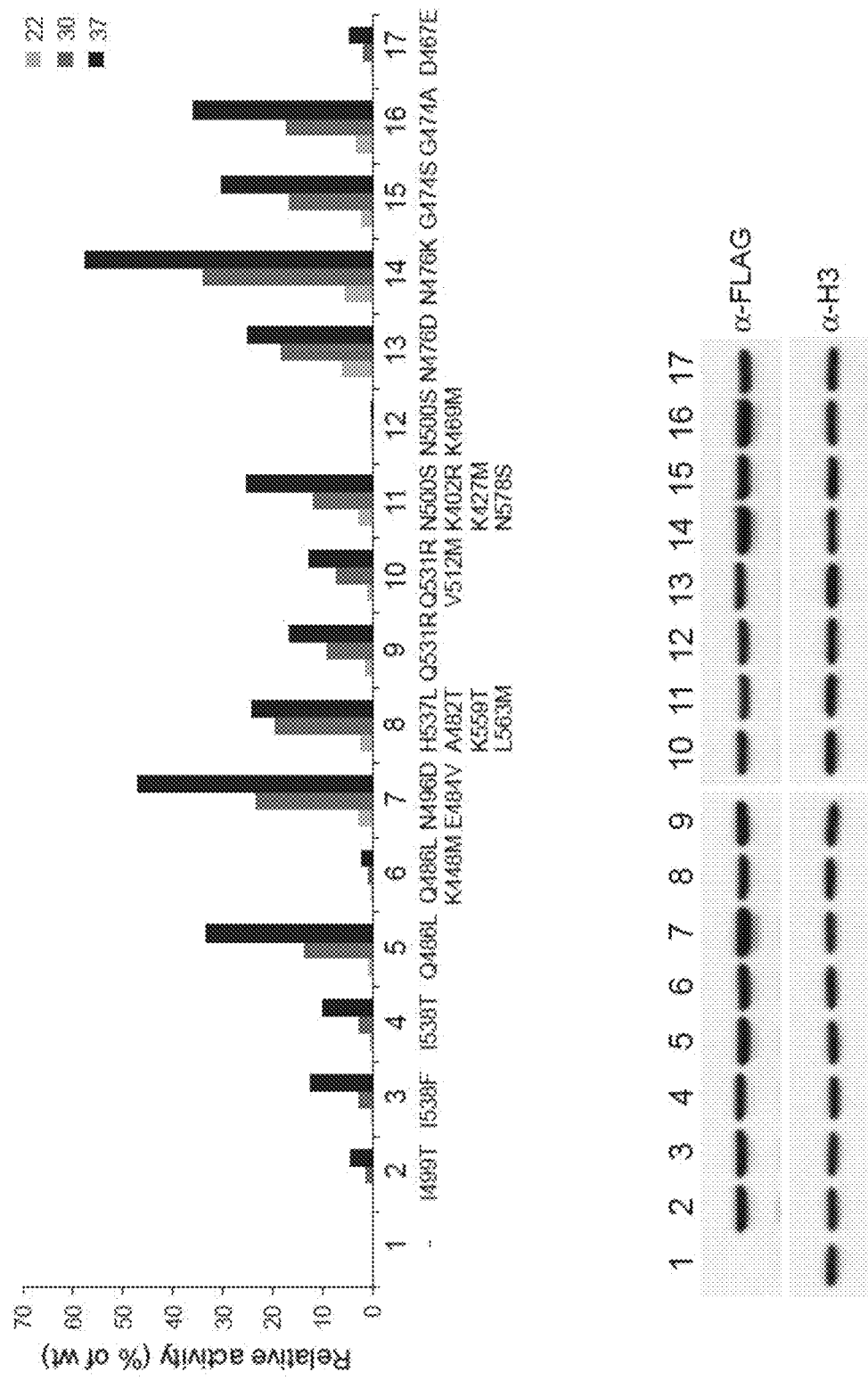
FIGS. 1A and 1B, depict the cleavage activity of zinc finger nucleases comprising the indicated cleavage domain mutants as described herein over a range of temperatures of the isolated mutants.
Figure 1B:
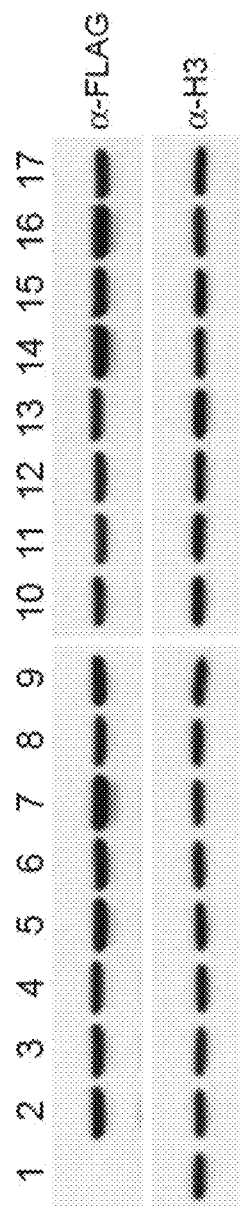

Disclosed herein are engineered cleavage half-domains and fusion polypeptides comprising these engineered cleavage half-domains useful for targeted cleavage of cellular chromatin and for targeted alteration of a cellular nucleotide sequence, e.g., by targeted cleavage followed by non-homologous end joining or by targeted cleavage followed by homologous recombination between an exogenous polynucleotide (comprising one or more regions of homology with the cellular nucleotide sequence) and a genomic sequence.

Exemplary engineered cleavage half-domains are shown in Table 4. The variants include mutations such that they form heterodimers with each other, but not homodimers. This increases the specificity of DNA cleavage and/or increases the concentration of the intended complex (by reducing or eliminating competition from homodimers). When incorporated into zinc finger nuclease fusion proteins, these variants induce gene modification at the intended target (both at an endogenous locus and when tested using an integrated GFP reporter assay) while significantly reducing genome wide DNA cleavage as compared to wild-type cleavage half-domains.

Thus, the engineered cleavage half-domains described herein significantly impair homodimer function, since forcing two copies of the same variant to interact reduces or abolishes gene modification. Reduced homodimer function provides improved ZFN cleavage specificity in vivo, without any decrease in either ZFN expression or the ability to stimulate modification of the desired target site.

In addition, disclosed herein are engineered cleavage half-domains with conditional activity. These conditional mutants can act either as homodimers or heterodimers, depending on the design. In certain embodiments, conditional activity refers to a change in cleavage activity based on temperature. Thus, these conditional mutants can be used in the development of cell lines or whole organisms such as plants wherein cleavage activity can be induced by the investigator at certain temperatures while being held in abeyance at other temperatures.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also International Patent Publication Nos. WO 98/53058; WO 98/53059; WO 98/53060; WO 02/016536; and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; and 6,200,759; and International Patent Publication Nos. WO 95/19431; WO 96/06166; WO 98/53057; WO 98/54311; WO 00/27878; WO 01/60970; WO 01/88197; and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain).

A "conditional mutation" is a mutation that has wild-type cleavage activity under certain permissive environmental conditions and a mutant cleavage activity under certain restrictive conditions. Conditional mutations may be cold sensitive, where the mutation results in an altered cleavage activity at cooler temperatures, but upon exposure to warmer temperatures, the cleavage activity returns more or less to wild-type. Conversely, conditional mutations may be heat sensitive (often termed "thermosensitive") where the wild type cleavage activity is seen at cooler temperatures but becomes altered upon exposure to warmer temperatures. Altered cleavage activity may be manifested as either increased or decreased activity.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eukaryotic" cells include, but are not limited to, fungal cells (such as yeast), plant cells, animal cells, mammalian cells and human cells.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields, et al., (1989) *Nature* 340:245-246; U.S. Pat. No. 5,585,245; and International Patent Publication No. WO 98/44350.

Engineered Cleavage Half-Domains

Engineered cleavage half-domains (also referred to as dimerization domain mutants) that minimize or prevent homodimerization are described for example in U.S. Patent Publication Nos. 2005/0064474; 2006/0188987; and 2008/0131962, incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. Numbering of amino acid residues in the FokI protein is according to Wah, et al., (1998) *Proc Nat'l Acad Sci USA* 95:10564-10569 (SEQ ID NO:57).

Described herein are engineered cleavage half-domains of FokI that exhibit increased activity and specificity as compared to previously described engineered FokI cleavage domains and/or wild-type cleavage domains. Exemplary mutant cleavage half-domains are shown in Table 3. Exemplary engineered cleavage domains are shown in Table 4. In certain embodiments, the cleavage half-domain includes mutations at least three amino acid residues at positions, as compared to wild-type. For example, in certain embodiments, the cleavage half-domain includes mutations at positions 486, 499 and 496. In other embodiments, the cleavage half-domain comprises mutations at positions 490, 538 and 537.

In one embodiment, the mutation at 490 replaces Glu (E) with Lys (K); the mutation at 538 replaces Ile (I) with Lys (K); the mutation at position 537 replaces His (H) with Lys (K) or Arg (R); the mutation at 486 replaced Gln (Q) with Glu (E); the mutation at position 499 replaces Ile (I) with Leucine (L); and the mutation at 496 replaces Asn (N) with Asp (D) or Glu (E). Specifically, the engineered cleavage half-domains described herein were prepared by mutating positions 490 (E→K), 538 (I→K), and 537 (H→K or H→R) in one cleavage half-domain to produce engineered cleavage half-domains designated "E490K:I538K:H537K" (KKK) or "E490K:I538K:H537R" (KKR) and by mutating positions 486 (Q→E), 499 (I→L) and 496 (N→D or N→E) in another cleavage half-domain to produce engineered cleavage half-domains designated "Q486E:I499L:N496E" (ELE) or "Q486E:I499L:N496D" (ELD). The engineered cleavage half-domains described herein form obligate heterodimer mutants in which aberrant cleavage is minimized or abolished, but activity as compared to wild-type is maintained. See Examples.

In other embodiments, the mutation at position 487 replaces Arg (R) with Asp (D) and the Asn (N) at position 496 is replaced with Asp (D) (to produce R487D:N496D or "DD") in one cleavage half-domain and by mutation of the wild-type Asp (D) at position 483 to a Arg (R) and mutation of the wild-type His (H) as position 537 with Arg (R) (to produce D483R:H537R or "RR") in the other cleavage half-domain. In still other embodiments, the mutation at 487 replaces Arg (R) with Asp (D); the mutation at position 499 replaces Ile (I) with Ala (A) and at position 496, the Asn (N) is replaced with Asp (D) (to produce "R487D:N496D:I499A" in one cleavage half domain) and by mutation at position 483 (D→R), 538 (I→V) and 537 (H→R) to produce "D483R:H537R:I538V:" at the other cleavage half domain (or DAD and RVR).

In other embodiments, mutations are made in other domains, for example at positions 418, 432, 441, 481, 523, 527 and/or 559. In certain embodiments, mutations made at positions 418 and 441, for example a replacement of the wild-type Ser (S) at position 418 with a Pro (P) residue and replacement of the wild-type Lys (K) at position 441 with a Glu (E), known as "S418P:K441E" or "Sharkey", or where Pro (P) replaces Ser (S) at 418, Leu (L) replaces Phe (F) at 432, Glu (E) replaces Lys (K) at 441, His (H) replaces Gln (Q) at 481, Tyr (Y) replaces His (H) at 523, Asp (D) replaces Asn (N) at 527 and Gln (Q) replaces Lys (K) at position 539, known as S418P:F432L:K441E:Q481H:H523Y:N527D: K539Q or Sharkey'. These mutations may be combined in any way with the domains listed above to produce, for example, the following FokI mutants:
- (a) EL-S: S418P:K441E:Q486E:I499L
- (b) KK-S: S418P:K441E:E490K:I538K
- (c) ELD-S: S418P:K441E:Q486E:N496D:I499L
- (d) KKK-S: S418P:K441E:E490K:H537K:I538K
- (e) KKR-S: S418P:K441E:E490K:H537R:I538K
- (f) DA-S: S418P:K441E:R487D:I499A
- (g) RV-S: S418P:K441E:D483R:I538V
- (h) DAD-S: S418P:K441E:R487D:N496D:I499A
- (i) RVR-S: S418P:K441E:D483R:H537R:I538V
- (j) DD-S: S418P:K441E:R487D:N496D
- (k) RR-S: S418P:K441E:D483R:H537R.

Engineered cleavage half-domains described herein can be prepared using any suitable method, for example, by site-directed mutagenesis of wild-type cleavage half-domains (FokI) as described in Example 5 of U.S. Patent Publication No. 2005/0064474 and Examples 5 and 38 of International Patent Publication WO 07/014275.

Fusion Proteins

The engineered cleavage half-domains described herein are advantageously used in fusion proteins with DNA binding proteins to specifically target sites for cleavage in any cell.

In certain embodiments, the DNA binding protein comprises a zinc finger protein (ZFP). Selection of target sites; ZFPs and methods for design and construction of fusion proteins (and polynucleotides encoding same) are known to those of skill in the art and described in detail in U.S. Patent Publication Nos. 2005/0064474 and 2006/0188987, incorporated by reference in their entireties herein.

In some embodiments, the DNA binding domain is an engineered domain from a TAL effector derived from the plant pathogen *Xanthomonas* (see, Miller, et al., (2010) *Nature Biotechnology*, December 22 [Epub ahead of print]; Boch, et al., (2009) *Science* 29 Oct. 2009 (10.1126/science.117881) and Moscou and Bogdanove, (2009) *Science* 29 Oct. 2009 (10.1126/science.1178817); see, also, U.S. Patent Publication No. 2011/0301073, the disclosure of which is hereby incorporated by reference in its entirety. In some embodiments, the TALE DNA binding domain is fused to a FokI cleavage as described, resulting in a TALE-nuclease (TALEN).

The nucleases (e.g., ZFNs) described herein may be delivered to a target cell by any suitable means. Methods of delivering proteins comprising zinc fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Fusion proteins (nucleases) as described herein may also be delivered using vectors containing sequences encoding one or more of the nucleases (e.g., ZFNs or TALENS). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties.

Conventional viral and non-viral based gene transfer methods can be used to introduce nucleic acids encoding nucleases (e.g., ZFNs or TALENS) comprising engineered cleavage domains in cells (e.g., mammalian cells) and target tissues. Such methods can also be used to administer such nucleic acids to cells in vitro. In certain embodiments, nucleic acids encoding the one or more nucleases are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel and Felgner, *TIBTECH* 11:211-217 (1993); Mitani and Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer and Perricaudet, *British Medical Bulletin* 51(1):31-44 (1995); Haddada, et al., in *Current Topics in Microbiology and Immunology* Doerfler and Böhm (eds.) (1995); and Yu, et al., *Gene Therapy* 1:13-26 (1994).

Methods of non-viral delivery of nucleic acids include electroporation, lipofection, microinjection, biolistics, virosomes, liposomes, immunoliposomes, polycation or lipid: nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.).

Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, International Patent Publication Nos. WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese, et al., *Cancer Gene Ther.* 2:291-297 (1995); Behr, et al., *Bioconjugate Chem.* 5:382-389 (1994); Remy, et al., *Bioconjugate Chem.* 5:647-654 (1994); Gao, et al., *Gene Therapy* 2:710-722 (1995); Ahmad, et al., *Cancer Res.* 52:4817-4820 (1992); U.S. Pat. Nos. 4,186,183; 4,217,344; 4,235,871; 4,261,975; 4,485,054; 4,501,728; 4,774,085; 4,837,028; and 4,946,787).

The use of RNA or DNA viral based systems for the delivery of nucleic acids encoding nucleases (e.g., ZFNs or TALENS) comprising engineered cleavage half-domains as described herein take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleases as described herein include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher, et al., *J. Virol.* 66:2731-2739 (1992); Johann, et al., *J. Virol.* 66:1635-1640 (1992); Sommerfelt, et al., *Virol.* 176:58-59 (1990); Wilson, et al., *J. Virol.* 63:2374-2378 (1989); Miller, et al., *J. Virol.* 65:2220-2224 (1991); International Patent Publication No. WO 1994/026877).

In applications in which transient expression of a ZFP fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West, et al., *Virology* 160:38-47 (1987); U.S. Pat. No. 4,797,368; International Patent Publication No. WO 93/24641; Kotin, *Human Gene Therapy* 5:793-801 (1994); Muzyczka, *J. Clin. Invest.* 94:1351 (1994). Construction of recombinant AAV vectors is described in a number of publications, including U.S. Pat. No. 5,173,414; Tratschin, et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar, et al., *Blood* 85:3048-305 (1995); Kohn, et al., *Nat. Med.* 1:1017-102 (1995); Malech, et al., *PNAS* 94:22 12133-12138 (1997)). PA317/pLASN was the first therapeutic vector used in a gene therapy trial. (Blaese, et al., *Science* 270:475-480 (1995)). Transduction efficiencies of 50% or greater have been observed for MFG-S packaged vectors. (Ellem, et al., *Immunol Immunother.* 44(1):10-20 (1997); Dranoff, et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner, et al., Lancet 351:9117 1702-3 (1998), Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad Ela, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman, et al., *Hum. Gene Ther.* 7:1083-9 (1998)). Additional examples of the use of adenovirus vectors for gene transfer in clinical trials include Rosenecker, et al., *Infection* 24:1 5-10 (1996); Sterman, et al., *Hum. Gene Ther.* 9:7 1083-1089 (1998); Welsh, et al., *Hum. Gene Ther.* 2:205-18 (1995); Alvarez, et al., *Hum. Gene Ther.* 5:597-613 (1997); Topf, et al., *Gene Ther.* 5:507-513 (1998); Sterman, et al., *Hum. Gene Ther.* 7:1083-1089 (1998).

In certain embodiments, the vector is an adenovirus vector. Thus, described herein are adenovirus (Ad) vectors for introducing heterologous sequences (e.g., zinc finger or TALE nucleases (ZFNs or TALENs)) into cells.

Non-limiting examples of Ad vectors that can be used in the present application include recombinant (such as E1-deleted), conditionally replication competent (such as oncolytic) and/or replication competent Ad vectors derived from human or non-human serotypes (e.g., Ad5, Ad11, Ad35, or porcine adenovirus-3); and/or chimeric Ad vectors (such as Ad5/35) or tropism-altered Ad vectors with engineered fiber (e.g., knob or shaft) proteins (such as peptide insertions within the HI loop of the knob protein). Also useful are "gutless" Ad vectors, e.g., an Ad vector in which all adenovirus genes have been removed, to reduce immunogenicity and to increase the size of the DNA payload. This allows, for example, simultaneous delivery of sequences encoding ZFNs and a donor sequence. Such gutless vectors are especially useful when the donor sequences include large transgenes to be integrated via targeted integration.

Replication-deficient recombinant adenoviral vectors (Ad) can be produced at high titer, and they readily infect a number of different cell types. Most adenovirus vectors are engineered such that a transgene replaces the Ad E1a, E1b, and/or E3 genes; subsequently the replication defective vector is propagated in cells that provide one or more of the deleted gene functions in trans. For example, human 293 cells supply E1 function. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman, et al., *Hum. Gene Ther.* 7:1083-1089 (1998)).

Additional examples of the use of adenovirus vectors for gene transfer in clinical trials include Rosenecker, et al., *Infection* 24:1 5-10 (1996); Welsh, et al., *Hum. Gene Ther.* 2:205-18 (1995); Alvarez, et al., *Hum. Gene Ther.* 5:597-613 (1997); Topf, et al., *Gene Ther.* 5:507-513 (1998).

In certain embodiments, the Ad vector is a chimeric adenovirus vector, containing sequences from two or more different adenovirus genomes. For example, the Ad vector can be an Ad5/35 vector. Ad5/35 is created by replacing one or more of the fiber protein genes (knob, shaft, tail, penton) of Ad5 with the corresponding fiber protein gene from a B group adenovirus such as, for example, Ad35. The Ad5/35 vector and characteristics of this vector are described, for example, in Ni, et al., (2005) *Hum Gene Ther* 16:664-677; Nilsson, et al., (2004) *Mol Ther* 9:377-388; Nilsson, et al., (2004) *J Gene Med* 6:631-641; Schroers, et al., (2004) *Exp Hematol* 32:536-546; Seshidhar, et al., (2003) *Virology* 311:384-393; Shayakhmetov, et al., (2000) *J Virol* 74:2567-2583; and Soya, et al., (2004), *Mol Ther* 9:496-509.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han, et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFN or TALEN nucleic acid (gene or cDNA), and re-infused back into the subject organism (e.g., patient). Various cell types suitable for ex vivo transfection are well known to those of skill in the art (see, e.g., Freshney, et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba, et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Iad (differentiated antigen presenting cells) (see Inaba, et al., *J. Exp. Med.* 176:1693-1702 (1992)). In some instances, the stem cells are induced pluripotent stem cells (iPSC).

Vectors (e.g., retroviruses, adenoviruses, liposomes, etc.) containing therapeutic ZFP or TALE nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34$^+$ cells, include adenovirus Type 35.

Vectors suitable for introduction of transgenes into immune cells (e.g., T-cells) include non-integrating lentivirus vectors. See, for example, Ory, et al., (1996) *Proc. Natl. Acad. Sci. USA* 93:11382-11388; Dull, et al., (1998) *J. Virol.* 72:8463-8471; Zuffery, et al., (1998) *J. Virol.* 72:9873-9880; Follenzi, et al., (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces*. Progeny, variants and derivatives of these cell lines can also be used.

Applications

The disclosed cleavage domains are advantageously used in combination with DNA-binding domains such as zinc finger proteins or TAL binding domains (resulting in ZFNs or TALENs respectively) to cleave DNA and minimize off-target site cleavage (as compared to DNA-binding domains comprising wild-type or homodimerizing cleavage domains). Cleavage can be at one or more region(s) of interest in cellular chromatin (e.g., at a desired or predetermined site in a genome, for example, in a gene, either mutant or wild-type); to replace a genomic sequence (e.g., a region of interest in cellular chromatin) with a homologous non-identical sequence (i.e., targeted recombination); to delete a genomic sequence by cleaving DNA at one or more sites in the genome, which cleavage sites are then joined by non-homologous end joining (NHEJ); to screen for cellular factors that facilitate homologous recombination; and/or to replace a wild-type sequence with a mutant sequence, or to convert one allele to a different allele. Such methods are described in detail, for example, in U.S. Patent Publication No. 2005/0064474; International Patent Publication No. WO 07/014275, incorporated by reference in their entireties herein.

Accordingly, the disclosed engineered cleavage half domains can be used in any ZFN or TALEN for any method in which specifically targeted cleavage is desirable and/or to replace any genomic sequence with a homologous, non-identical sequence. For example, a mutant genomic sequence can be replaced by its wild-type counterpart, thereby providing methods for treatment of e.g., genetic disease, inherited disorders, cancer, and autoimmune disease. In like fashion, one allele of a gene can be replaced by a different allele using the methods of targeted recombination disclosed herein. Indeed, any pathology dependent upon a particular genomic sequence, in any fashion, can be corrected or alleviated using the methods and compositions disclosed herein.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Such methods also allow for treatment of infections (viral or bacterial) in a host (e.g., by blocking expression of viral or bacterial receptors, thereby preventing infection and/or spread in a host organism) to treat genetic diseases.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. See, U.S. Patent Application No. 2008/015996. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4.

Thus, heterodimeric cleavage domain variants as described herein provide broad utility for improving ZFN specificity in gene modification applications. These variant cleavage domains may be readily incorporated into any existing ZFN by either site directed mutagenesis or subcloning to improve the in vivo specificity of any ZFN dimers.

As noted above, the compositions and methods described herein can be used for gene modification, gene correction, and gene disruption. Non-limiting examples of gene modification includes homology directed repair (HDR)-based targeted integration; HDR-based gene correction; HDR-based gene modification; HDR-based gene disruption; NHEJ-based gene disruption and/or combinations of HDR, NHEJ, and/or single strand annealing (SSA). Single-Strand Annealing (SSA) refers to the repair of a double strand break between two repeated sequences that occur in the same orientation by resection of the DSB by 5'-3' exonucleases to expose the 2 complementary regions. The single-strands encoding the 2 direct repeats then anneal to each other, and the annealed intermediate can be processed such that the single-stranded tails (the portion of the single-stranded DNA that is not annealed to any sequence) are be digested away, the gaps filled in by DNA Polymerase, and the DNA ends rejoined. This results in the deletion of sequences located between the direct repeats.

Compositions comprising cleavage domains (e.g., ZFNs) and methods described herein can also be used in the treatment of various genetic diseases and/or infectious diseases.

The compositions and methods can also be applied to stem cell based therapies, including but not limited to: correction of somatic cell mutations by short patch gene conversion or targeted integration for monogenic gene therapy; disruption of dominant negative alleles; disruption of genes required for the entry or productive infection of pathogens into cells; enhanced tissue engineering, for example, by modifying gene activity to promote the differentiation or formation of functional tissues; and/or disrupting gene activity to promote the differentiation or formation of functional tissues; blocking or inducing differentiation, for example, by disrupting genes that block differentiation to promote stem cells to differentiate down a specific lineage pathway, targeted insertion of a gene or siRNA expression cassette that can stimulate stem cell differentiation, targeted insertion of a gene or siRNA expression cassette that can block stem cell differentiation and allow better expansion and maintenance of pluripotency, and/or targeted insertion of a reporter gene in frame with an endogenous gene that is a marker of pluripotency or differentiation state that would allow an easy marker to score differentiation state of stem cells and how changes in media, cytokines, growth conditions, expression of genes, expression of siRNA, shRNA or miRNA molecules, exposure to antibodies to cell surface markers, or drugs alter this state; somatic cell nuclear transfer, for example, a patient's own somatic cells can be isolated, the intended target gene modified in the appropriate manner, cell clones generated (and quality controlled to ensure genome safety), and the nuclei from these cells isolated and transferred into unfertilized eggs to generate patient-specific hES cells that could be directly injected or differentiated before engrafting into the patient, thereby reducing or eliminating tissue rejection; universal stem cells by knocking out MHC receptors (e.g., to generate cells of diminished or altogether abolished immunological identity). Cell types for this procedure include but are not limited to, T-cells, B cells, hematopoietic stem cells, and embryonic stem cells. Additionally, induced pluripotent stem cells (iPSC) may be used which would also be generated from a patient's own somatic cells. Therefore, these stem cells or their derivatives (differentiated cell types or tissues) could be potentially engrafted into any person regardless of their origin or histocompatibility.

The compositions and methods can also be used for somatic cell therapy (e.g., autologous cell therapy and/or universal T-cell by knocking out MHC or viral receptors, see above), thereby allowing production of stocks of T-cells that have been modified to enhance their biological properties. Such cells can be infused into a variety of patients independent of the donor source of the T-cells and their histocompatibility to the recipient.

In addition to therapeutic applications, the increased specificity provided by the variants described herein when used in ZFNs can be used for crop engineering, cell line engineering and the construction of disease models. The obligate heterodimer cleavage half-domains provide a straightforward means for improving ZFN properties, especially when homodimer activity limits efficacy.

The engineered cleavage half domains described can also be used in gene modification protocols requiring simultaneous cleavage at multiple targets either to delete the intervening region or to alter two specific loci at once. Cleavage at two targets would require cellular expression of four ZFNs, which could yield potentially ten different active ZFN combinations. For such applications, substitution of these novel variants for the wild-type nuclease domain would eliminate the activity of the undesired combinations and reduce chances of off-target cleavage. If cleavage at a certain desired DNA target requires the activity of the ZFN pair A+B, and simultaneous cleavage at a second desired DNA target requires the activity of the ZFN pair X+Y, then use of the mutations described herein can prevent the pairings of A with A, A with X, A with Y and so on. Thus, these FokI mutations decrease non-specific cleavage activity as a result of "illegitimate" pair formation and allow the generation of more efficient orthogonal mutant pairs of ZFNs (see co-owned patent U.S. Patent Publication Nos. 2008/0131962 and 2009/0305346).

In addition to the applications described for the engineered cleavage half domains, there are also numerous applications for the conditional mutations described herein. The identified cold-sensitive mutations can be used to create transgenic organisms carrying an integrated copy of the nucleic acid encoding the mutations. Plants carrying such mutations would display the mutant phenotype such that the cleavage activity would be quiescent at cooler temperatures. Upon a shift to higher temperatures, the fusion would display active cleavage activity. These mutant organisms could be used to create lines for breeding purposes where lines containing the cold sensitive mutation could be crossed to lines carrying a certain target such that when the progeny of the cross were shifted to higher temperatures, cleavage of the target would occur. This would increase the efficiency of such processes because it would reduce the number of plant transformations with either donor or fusion protein that would be required to achieve a desired result. The same type of scenario can also be envisioned for thermo sensitive conditional mutants.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure.

EXAMPLES

Example 1: Preparation of ZFNs

ZFNs targeted to CCR5, 53BP1, GR, KDR, RIPK1, CXCR4 and PD-1 were designed and incorporated into plasmids vectors essentially as described in Urnov, et al., (2005) *Nature* 435(7042):646-651, Perez, et al., (2008) *Nature Biotechnology* 26(7): 808-816, and U.S. Patent Publication No. 2008/0131962 or were obtained from Sigma Aldrich. These ZFNs were constructed and tested by ELISA and the Surveyor™ (Transgenomics) Cel-1 assay ("Cel-1") as described in Miller, et al., (2007) *Nat. Biotechnol.* 25:778-785 and U.S. Patent Publication No. 2005/0064474 and International Patent Publication No. WO 2005/014791. In addition, see U.S. Patent Publication No. 2008/0188000 for ZFNs targeted to GR, and U.S. Provisional Application No. 61/281,432 relating to ZFNs targeted to PD-1, U.S. Patent Publication No. 2008/0159996 relating to CCR5-specific ZFNs and U.S. Pat. No. 8,871,905 relating to CXCR4-specific ZFNs.

Specific examples of ZFPs targeted to RIPK1, KDR and 53BP1 are disclosed in Table 1. The first column in this table is an internal reference name (number) for a ZFP. "F" refers to the finger and the number following "F" refers to which zinc finger (e.g., "F1" refers to finger 1). Table 2 lists target binding sites on the target genes. Nucleotides in the target site that are contacted by the ZFP recognition helices are indicated in uppercase letters; non-contacted nucleotides indicated in lowercase.

TABLE 1

ZFP designs for 53BP1, KDR and RIPK1

| SBS # (target) | F1 | F2 | F3 | F4 | F5 | F6 |
|---|---|---|---|---|---|---|
| 18346 (53BP1) | RSDHLST (SEQ ID NO: 1) | TSANLSR (SEQ ID NO: 2) | RSDNLSE (SEQ ID NO: 3) | TSGSLTR (SEQ ID NO: 4) | N/A | N/A |
| 18347 (53BP1) | QSGALAR (SEQ ID NO: 5) | RSDNLTR (SEQ ID NO: 6) | QSGNLAR (SEQ ID NO: 7) | QSGNLAR (SEQ ID NO: 7) | QSGHLQR (SEQ ID NO: 8) | QSSDLRR (SEQ ID NO: 9) |
| 19135 (KDR) | RSDTLSE (SEQ ID NO: 10) | TSGSLTR (SEQ ID NO: 4) | RSDNLSR (SEQ ID NO: 11) | QNAHRTT (SEQ ID NO: 12) | QSSNLAR (SEQ ID NO: 13) | RSDDLTR (SEQ ID NO: 14) |
| 19136 (KDR) | DRSHLSR (SEQ ID NO: 15) | QSGNLAR (SEQ ID NO: 7) | DNPNLNR (SEQ ID NO: 16) | RSDDLSR (SEQ ID NO: 17) | RSDNLSE (SEQ ID NO: 3) | RNAHRIN (SEQ ID NO: 18) |
| 19119 (RIPK1) | RSANLTR (SEQ ID NO: 19) | RSDNLSE (SEQ ID NO: 3) | ASKTRKN (SEQ ID NO: 20) | DRSNLSR (SEQ ID NO: 21) | TSANLSR (SEQ ID NO: 2) | N/A |
| 19120 (RIPK1) | QSGALAR (SEQ ID NO: 5) | QSGNLAR (SEQ ID NO: 7) | RSDHLSA (SEQ ID NO: 22) | QSGHLSR (SEQ ID NO: 23) | N/A | N/A |
| 19123 (RIPK1) | TSGSLSR (SEQ ID NO: 24) | QSSDLRR (SEQ ID NO: 9) | RSDTLSA (SEQ ID NO: 25) | DNSNRIK (SEQ ID NO: 26) | RSAALSR (SEQ ID NO: 27) | QSGDLTR (SEQ ID NO: 28) |
| 19124 (RIPK1) | QSGHLSR (SEQ ID NO: 23) | RSDSLSA (SEQ ID NO: 29) | DRSNLTR (SEQ ID NO: 30) | RSDNLSQ (SEQ ID NO: 31) | ASNDRKK (SEQ ID NO: 32) | N/A |
| 19121 (RIPK1) | RSDNLSR (SEQ ID NO: 11) | DSSTRKK (SEQ ID NO: 33) | RSDNLSV (SEQ ID NO: 34) | DRSHLAR (SEQ ID NO: 35) | QSGHLSR (SEQ ID NO: 23) | N/A |
| 19122 (RIPK1) | QRSNLVR (SEQ ID NO: 36) | QSSDLTR (SEQ ID NO: 37) | GNVDLIE (SEQ ID NO: 38) | RSSNLSR (SEQ ID NO: 39) | RSDSLSV (SEQ ID NO: 40) | TNHNRKT (SEQ ID NO: 41) |

TABLE 2

ZFN Target sites

| SBS# (target) | Target site |
|---|---|
| 18346 (53BP1) | ttGTTCAGGATTGGacacaacatcctag_ (SEQ ID NO: 42) |
| 18347 (53BP1) | caGCTGGAGAAGAAcGAGGAGacggtaa_ (SEQ ID NO: 43) |

TABLE 2-continued

ZFN Target sites

| SBS# (target) | Target site |
|---|---|
| 19135 (KDR) | ctGCGGATAGTGAGGTTCCGgacccat_ (SEQ ID NO: 44) |
| 19136 (KDR) | tgAGGAAGGAGGACGAAGGCctctacac_ (SEQ ID NO: 45) |
| 19119 (RIPK1, pair A) | atGATGACGCCCAGGAGatcaccaccc_ (SEQ ID NO: 46) |
| 19120 (RIPK1, pair A) | gaGGAAGGGAAGTActccctggtgatgg_ (SEQ ID NO: 47) |
| 19123 (RIPK1, pair B) | gtGCAGTGAACCAGGCTGTTctgtggct_ (SEQ ID NO: 48) |
| 19124 (RIPK1, pair B) | gtTCCCAGgGACTTGGGAtgggtcctgt_ (SEQ ID NO: 49) |
| 19121 (RIPK1, pair C) | aaGGAGGCAAGGCCGAGgtctgcgatct_ (SEQ ID NO: 50) |
| 19122 (RIPK1, pair C) | aaGATGTGGAGCAAACTGAAtaatgaag_ (SEQ ID NO: 51) |

Example 2: Genetic Screening for Mutant FokI ZFNs

Using *Saccharomyces cerevisiae* as a model system, we isolated ZFN mutants displaying a cold-sensitive phenotype with cleavage activity that is severely diminished at lower temperature but adequate at higher ones. Cold-sensitive mutations are particularly interesting because historically they have been shown to occur in genes encoding subunits of multimeric protein complexes. These mutations affect protein-protein interactions predominantly at low temperature. Thus, isolating this class of mutants revealed non-null mutations that identify important residues within the dimerization interface.

Single-stranded annealing (SSA)-reporter strain and mutant library construction was performed as follows. Random mutagenesis of the FokI nuclease domain was done using error-prone PCR and the library of mutants was constructed by gap repair in *Saccharomyces cerevisiae*. Briefly, the reporter strain was co-transformed with the mutagenized PCR fragment (FokI domain) and a linearized plasmid vector prepared such that the ends of the vector shared DNA sequence with the ends of the PCR fragment. Homologous recombination between the vector and the PCR fragment occurred at a high frequency and resulted in a collection of yeast transformants, containing a mutated ZFN expression vector. The zinc finger domain of the nuclease binds to the human CCR-5 gene (designated 8266) and is described in detail in U.S. Patent Publication No. 2008/0159996.

The library was then screened or selected for phenotypes of interest in budding yeast, essentially as described in U.S. Patent Publication No. 2009/0111119. Briefly, two independent SSA reporter constructs were integrated in the genome of budding yeast. Both reporters contain a binding site for a homodimer of the 8266 ZFN. The MEL1 SSA reporter contains both positive and negative selection markers. The URA3 gene is used for positive selection in ura-media and for negative selection using 5-Fluoroorotic Acid (5-FOA). The KanMX cassette confers dominant resistance to geneticin (G418). Reconstitution of the MEL1 gene following SSA was detected using chromogenic substrates [p-Nitrophenyl α-D-galactopyranoside (PNPG) or 5-Bromo-4-chloro-3-indoxyl-alpha-D-galactopyranoside (X-a-Gal)]. The PHO5 SSA reporter contains the positive selection cassette NatMX conferring dominant resistance to nourseothricin (NAT) and reconstitution of the PHO5 gene was detected using chromogenic substrates [p-Nitrophenyl phosphate disodium (PNPP) or x-phosphate p-toluidine salt (X-Phos)]. Therefore, a DNA double-stranded break (DSB) induced by a functional 8266 ZFN induced SSA resulted in reconstitution of the reporter genes and elimination of positive and negative selection markers.

The genetic screen for FokI mutants was conducted as follows. First, galactose-inducible expression of the ZFNs was performed at the non-permissive temperature of 22° C. Following recovery, the cells were incubated in Kan (G418), NAT and ura-media to eliminate all active ZFNs. This step selected for potential cold-sensitive mutants as well as for inactive ZFN.

Second, the cells were shifted to 37° C. (permissive temperature) and plated on media containing 5-FOA and X-Phos. Only cells containing a cold-sensitive ZFN formed blue colonies. The plasmids from these cells were then isolated and retransformed into the reporter strain to confirm the cold-sensitive phenotype. The resulting mutations were identified by direct sequencing of the FokI domain.

Table 3 shows various mutants identified by the screen. Mutations predicted to confer cold sensitivity are indicated in the first column (based on proximity to the dimer interface in ZFNs).

TABLE 3

ZFN cold-sensitive mutants

| Mutations | # isolates |
|---|---|
| I499T | 1 |
| I538F | 1 |
| I538T | 3 |

TABLE 3-continued

ZFN cold-sensitive mutants

| Mutations | | | | # isolates |
|---|---|---|---|---|
| Q486L | | | | 2 |
| Q486L | K448M | | | 4 |
| N496D | E484V | | | 3 |
| H537L | A482T | K559T | L563M | 1 |
| Q531R | | | | 2 |
| Q531R | V512M | | | 1 |
| N500S | K402R | K427M | N578S | 1 |
| N500S | K469M | | | 1 |
| N476D | | | | 1 |
| N476K | | | | 1 |
| G474S | | | | 4 |
| G474A | | | | 5 |
| D467E | | | | 1 |

Activity (relative to wild-type) of the cold sensitive cleavage activities of the isolated mutants is shown in FIG. 1A. The reporter strain was transformed with the isolated mutant vectors, divided into three cultures, and incubated at 22° C., 30° C., and 37° C. Following expression, the activity of the mutants was determined and reported as a fraction of the activity of the wild-type ZFN. The increase in ZFN cleavage activity correlated with elevated temperature of incubation indicates that the isolated mutants are cold-sensitive.

Example 3: Design of Novel Engineered FokI Cleavage Half-Domains

Using the ZFN structure model described in Miller, et al., (2007) Nat. Biotech. 25(7):778-85, we mapped the position of the mutations tested in Example 2 and found out that two of the mutated residues (N496 and H537) face each other on the dimer interface and are found in close proximity. Modelization of those mutations also showed that H537R and N496D mutations would likely form salt-bridges and strengthen the dimerization interface. Table 4 shows the nomenclature of various mutants tested.

TABLE 4

Engineered Cleavage Domain Nomenclature

| Cleavage domain designation | Mutations (wildtype residue-position-mutant residue) |
|---|---|
| EL | Q486E + I499L |
| ELD | Q486E + I499L + N496D |
| ELE | Q486E + I499L + N496E |
| KK | E490K + I538K |
| KKK | E490K + I538K + H537K |
| KKR | E490K + I538K + H537R |
| REL | H537R + Q486E + I499L |
| DKK | N496D + E490K + I538K |
| DD | R487D + N496D |
| DAD | R487D + N496D + I499A |
| RR | D483R + H537R |
| RVR | D483R + H537R + 538V |
| KIK* | E490K + H537K |
| KIR* | E490K + H537R |
| DA** | R487D + I499A |
| EA** | Q486E + I499A |
| KV** | E490K + I538V |
| RV** | D483R + I538V |
| Sharkey*** | S418P + K441E |
| EL-Sharkey | Q486E + I499L + S418P + K441E |
| KK-Sharkey | E490K + I538K + S418P + K441E |
| ELD-Sharkey | Q486E + I499L + N496D + S418P + K441E |
| KKK-Sharkey | E490K + I538K + H537K + S418P + K441E |
| KKR-Sharkey | E490K + I538K + H537R + S418P + K441E |

TABLE 4-continued

Engineered Cleavage Domain Nomenclature

| Cleavage domain designation | Mutations (wildtype residue-position-mutant residue) |
|---|---|
| DA-Sharkey | R487D + I499A + S418P + K441E |
| EA-Sharkey | Q486E + I499A + S418P + K441E |

*Note:
For the KIK and KIR mutants, the amino acid at position 538 is an isoleucine as is the wild type. The nomenclature for KIK and KIR uses the 'I' to distinguish these mutants from the KK mutants.
**Described in Szczepek et al., (2007) Nature Biotechnology 25(7) p. 786-93.
***Described in Guo et al., ibid Various pairwise combinations of the triple mutants (e.g., ELD:KKK, ELD:KKR, ELE:KKK and ELE:KKR) were compared for cleavage activity against EL:KK pairs (EL:KK mutants are described in U.S. Patent Publication No. 2008/0131962) in a variety of ZFN backgrounds. The ZFN-containing plasmids were then nucleofected into K562 or PMBC cells. To determine the ZFN activity at the appropriate locus, Cel-1 mismatch assays were performed essentially as per the manufacturer's instructions (Trangenomic SURVEYOR™). Cells were harvested and chromosomal DNA prepared using a Quickextract™ Kit according to manufacturer's directions (Epicentre®). The appropriate region of the targeted locus was PCR amplified using Accuprime™ High-fidelity DNA polymerase (Invitrogen). PCR reactions were heated to 94° C., and gradually cooled to room temperature. Approximately 200 ng of the annealed DNA was mixed with 0.33 μL Cel-1 enzyme and incubated for 20 minutes at 42° C. Reaction products were analyzed by polyacrylamide gel electrophoresis in 1× Tris-borate-EDTA buffer.

Figures 2A, 2B:
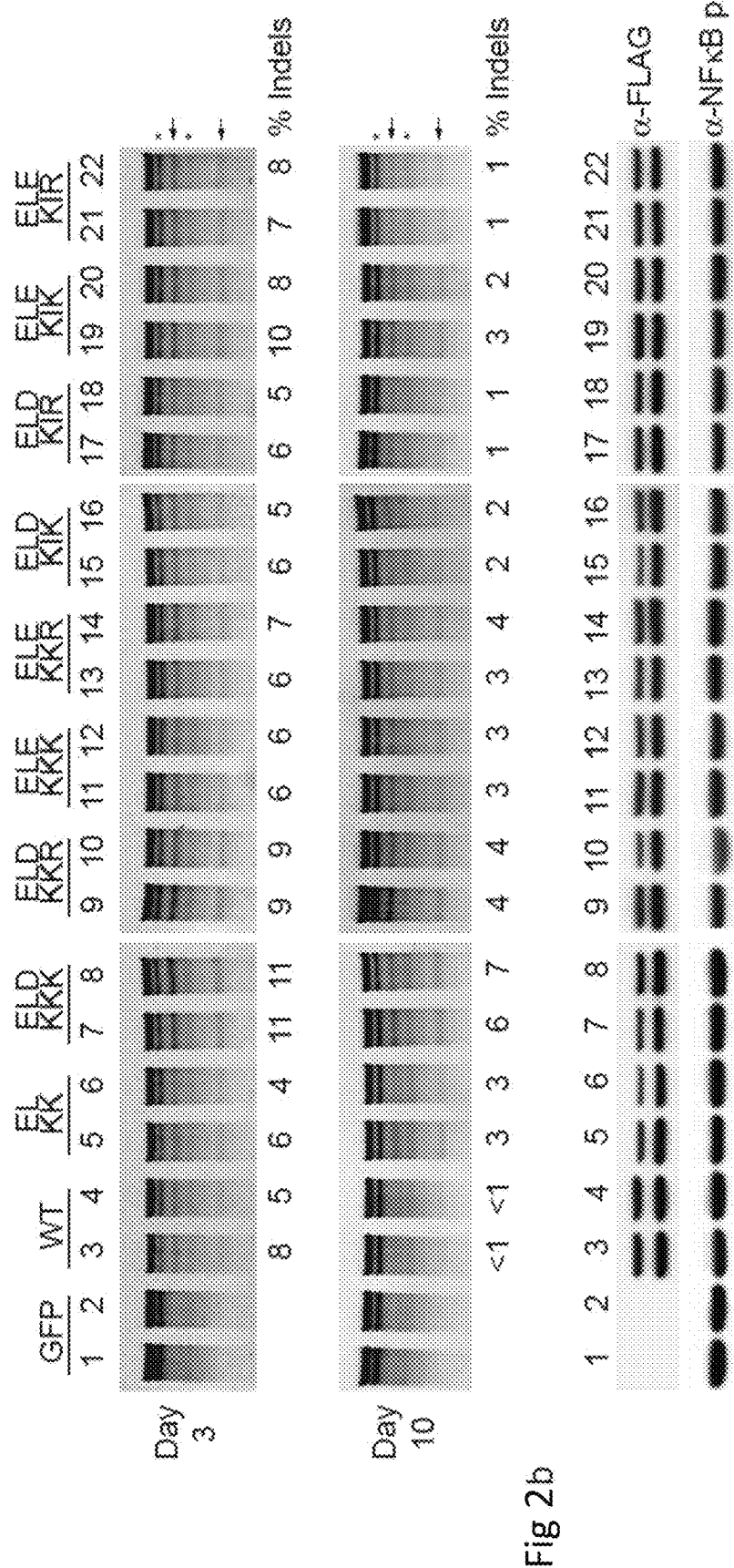
FIGS. 2A and 2B depict the activity of the ZFN variants ELD:KKK and ELD:KKR in the 53BP1-specific ZFN background.
Figure 3A:
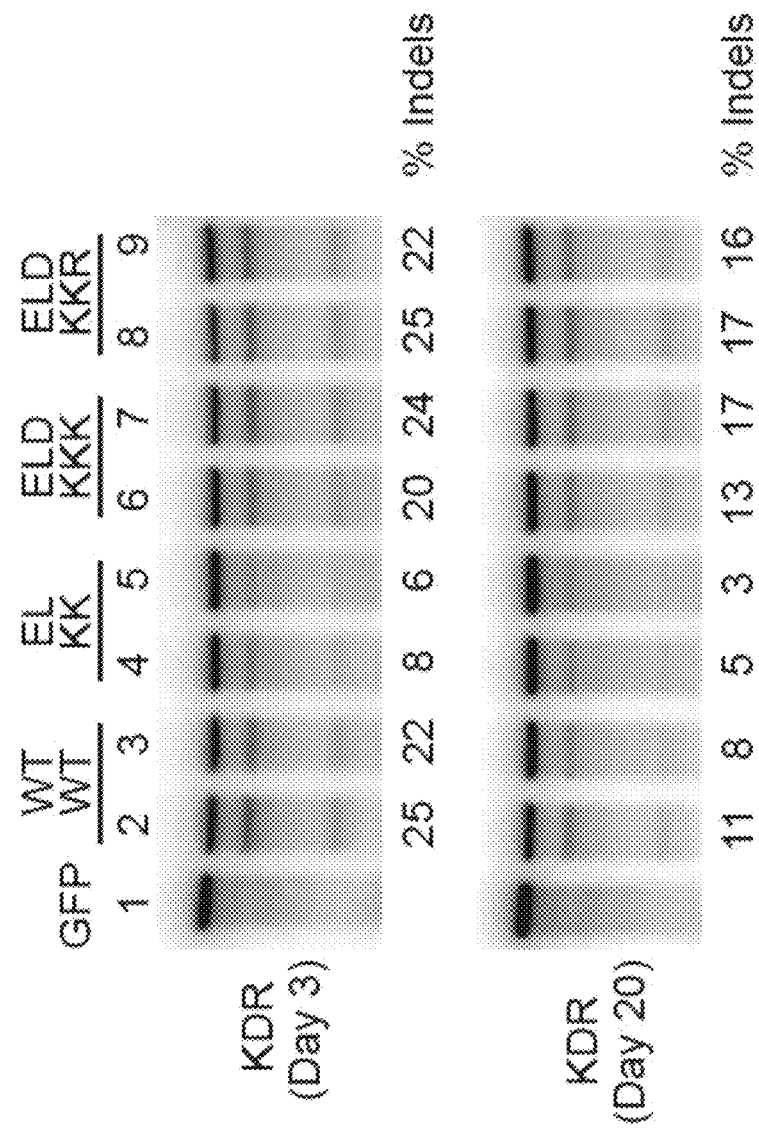
FIGS. 3A and 3B, show activity of mutants in the KDR-specific ZFN background.
Figure 3B:
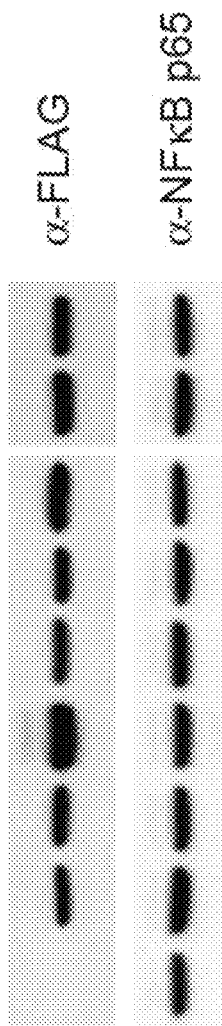
Figure 4:
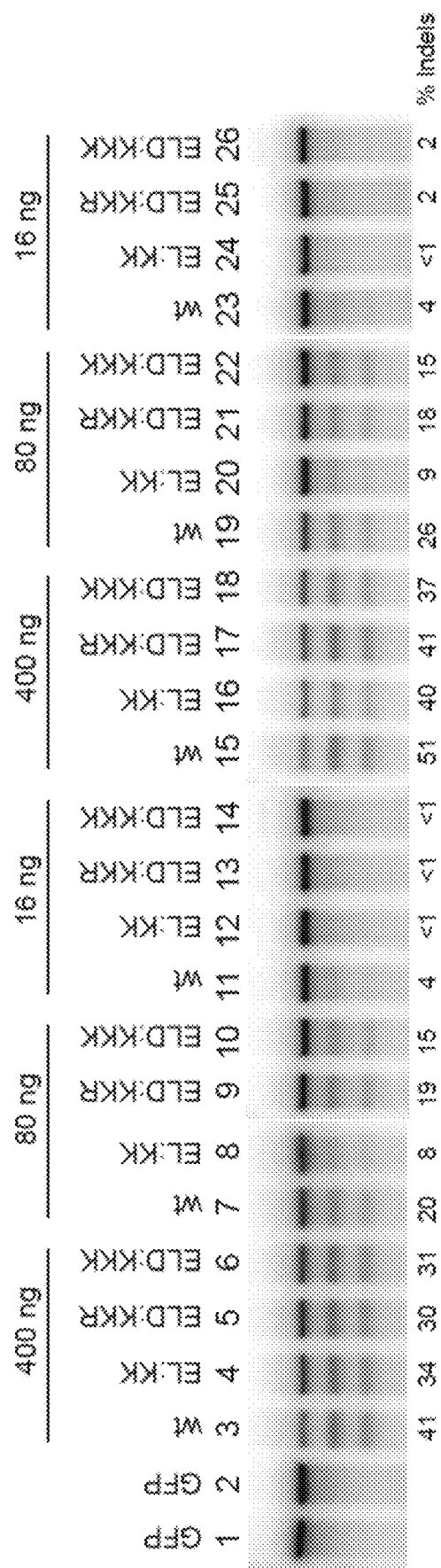
FIG. 4 depicts the activity of ZFN variants ELD:KKK and ELD:KKR in the GR-specific ZFN background, where activity is determined by the Cel-I assay as described above for FIG. 2. The figure shows the results from two sets of samples for each condition. Lanes 1-14 are one set, and lanes 15-26 are the second set. The novel mutants are more active than the original obligate heterodimeric EL:KK at limiting ZFN doses for highly active ZFNs (compare lane 8 with lanes 9 and 10 and lane 20 with lanes 21 and 22). Decreasing amounts of GR-targeting ZFNs (shown along the top of the panel) were nucleofected in K562s, the cells were harvested 3 days post-transfection, and the Cel-1 assay was used to determine the frequency of ZFN-induced indels.

As shown in FIGS. 2 to 5, the various combinations of the triple mutants are more active than the original obligate heterodimeric ZFN (EL:KK). In particular, FIG. 2 shows Cel-1 assay results of ZFN variants ELD:KKK, ELD:KKR, ELE:KKK, ELE:KKR, ELD:KIK, ELD:KIR, ELE:KIK and ELE:KIR in ZFNs targeted to 53BP1 3 and 10 days post-transfection of the ZFNs into K562 cells. FIG. 3 shows Cel-1 assay results of ZFN variants ELD:KKK and ELD:KKR in ZFNs targeted to KDR and 20 days post-transfection of the ZFNs into K562 cells. FIG. 4 shows Cel-1 assay results of the ELD; KKR and ELD:KKK FokI engineered cleavage domains in the context of GR-specific ZFNs in K562 cells. FIG. 4 also shows the cleavage activities using decreasing amounts of expression plasmid for transfection (from 400 ng to 16 ng), with two different sets of samples (lanes 1-14 and lanes 15-26). These results show that at 80 ng of input expression plasmid, the ELD:KKR and ELF:KKK mutants were both more active that the EL:KK mutants (compare lane 8 with lanes 9 and 10 and lane 20 with lanes 21 and 22).

Figure 5B:
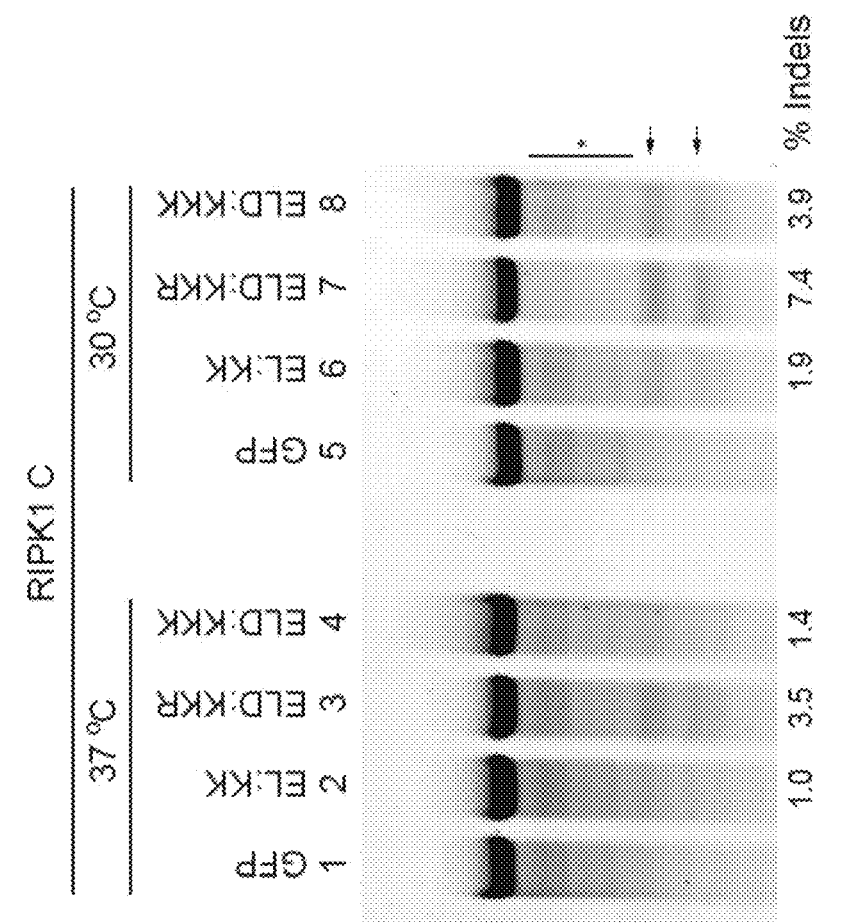
FIGS. 5A and 5B depict the activity of mutants in three different RIPK1-specific ZFN pairs (pairs A, B and C).
Figure 5A:
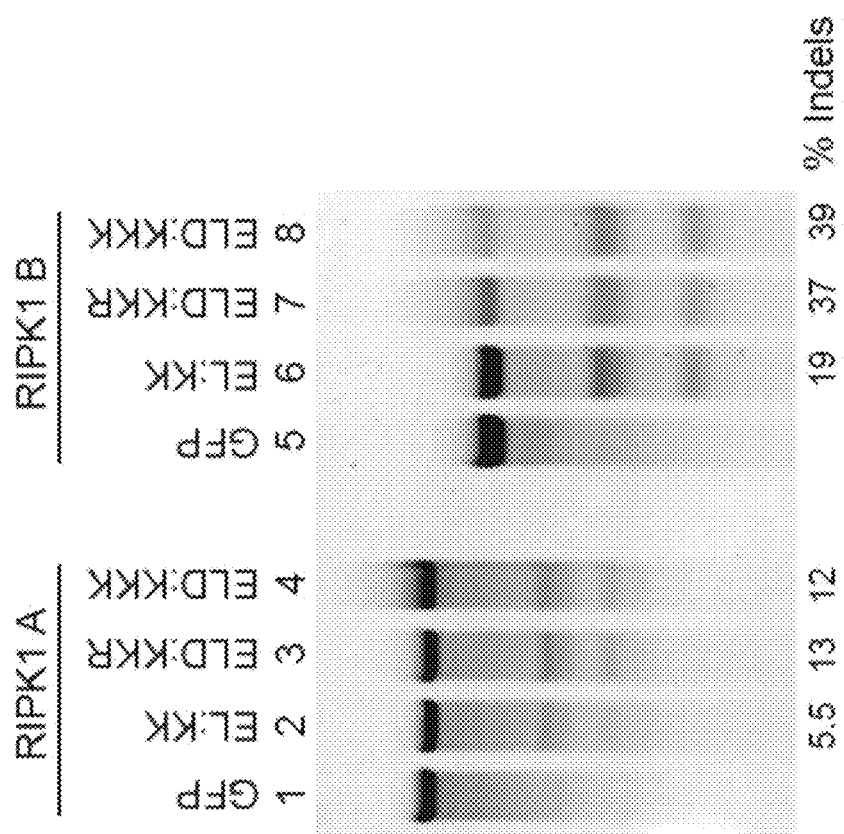

FIG. 5 shows the cleavage activities of the ELD:KKR and ELD:KKK mutants in three different RIPK1-specific ZFN backgrounds. The new mutants were both more active that the EL:KK mutant in RIPK1 pair A and RIPK1 pair B. In FIG. 5B, the new mutants in the pair C background were tested at both 37° C. and 30° C. where activity of all ZFP pairs was found to be increased at 30° C. (see U.S. Patent Publication No: 2009/0111119).

Example 4: Activity of Engineered Cleavage Domains as Homodimers

The new mutants were also tested for their ability to actively cleave DNA as forced homodimers. In these assays, the zinc finger binding domains are fused to a FokI cleavage domain that is the same in both members of the pair. Thus, in order to observe any activity, the FokI domain must homodimerize with itself ("forced homodimerization"). Forced homodimerization of CCR5-targeting ZFNs was assayed by nucleofection of FokI variants in K562 cells (see FIG. 6) and the Cel-1 assay was used to determine the frequency of ZFN-induced indels at the CCR5 heterodimer target, a CCR5-L ZFN homodimer (ABLIM2), and a CCR5-R homodimer (PGC) off-target sites. For these experiments, the mutations were made in the CCR5-specific 8266 and 8196z pair and then tested. Thus, in the lanes labeled "WT", the 8266/8196z pair was used. Then for each mutant pair tested, a similar pair was made with the indicated mutations, so the EL:EL lanes indicate a pair containing 8266-EL and 8196z-EL and so on.

Figures 6A, 6B:
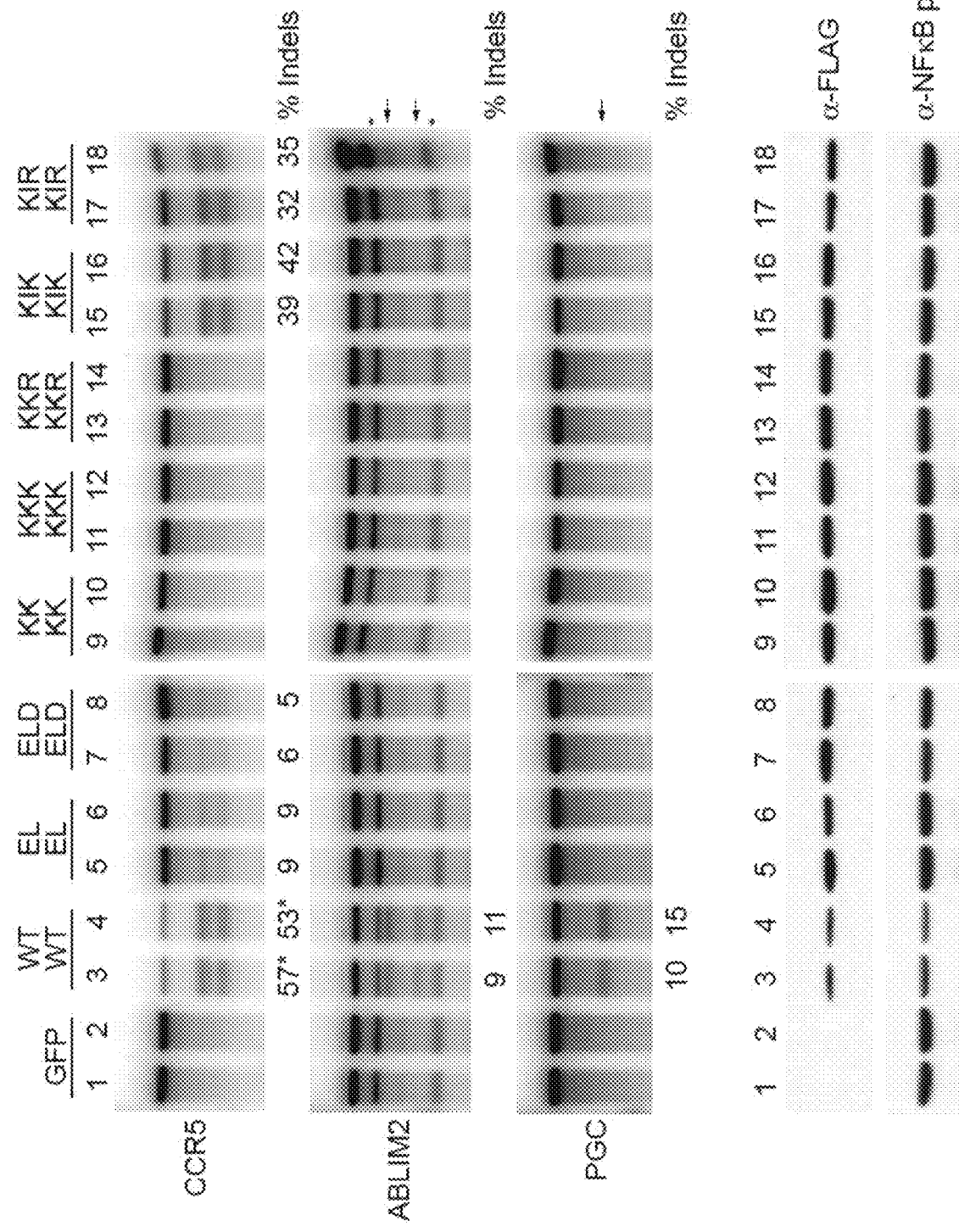
FIGS. 6A and 6B show the Cel-1 activity assay results (as described above for FIG. 2) of CCR-5-specific ZFN pairs (see, U.S. Patent Publication No. 2008/0159996).

As can be seen from FIG. 6, whereas the KK, KKK, and KKR homodimers show no detectable cleavage activity at the CCR5 heterodimer target site, there is limited cutting by the EL:EL and ELD:ELD homodimers. The ELD:ELD variants have an approximately 1.5 fold lower activity as compared to EL:EL indicating increased specificity. Importantly, examination of the known off-target sites ABLIM2 and PGC show no detectable cleavage activity by any of the mutants.

In order to further confirm the improvement in specificity of the ELD cleavage domain, these same forced homodimers were tested in decreasing concentrations in K562 cells. As can be seen from FIG. 7, at all DNA concentration tested, ELD:ELD displays a lower homodimer activity as compared to EL:EL. Forced GR-specific ZFN homodimers were also tested (see FIG. 8) and there was no cleavage activity detectable. In some embodiments, the I499A mutant was used to replace the I449L mutation to further decrease any potential ELD homodimerization. In this case, forced homodimerization of the EAD CCR5 specific ZFN gave no detectable cleavage activity.

Figure 9:
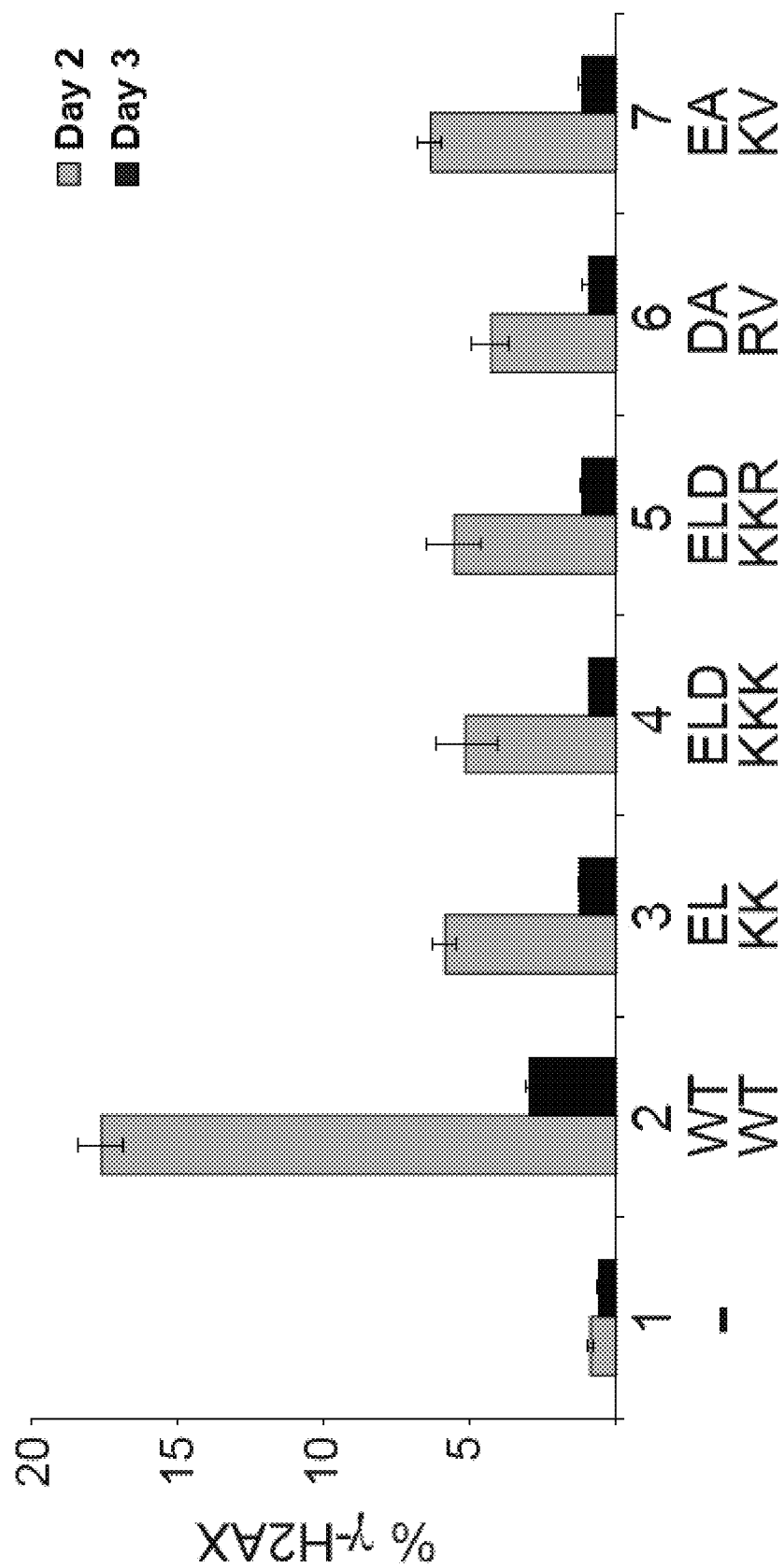
FIG. 9 depicts flow cytometry data for K562 cells treated with the indicated constructs in the GR targeting ZFN background stained with antibodies against γ-H2AX which targets DSBs. The percent of positive cells is indicated. The percent of DSBs observed for all the FokI mutant pairs was much less than for the wild-type FokI.

In addition, these cells were also tested for DSBs using an antibody specific for γ-H2AX which accumulates at DSB sites in the genome. The stained cells were sorted by flow cytometry, and the results are shown in FIG. 9. As can be seen from the figure, there is very little staining except for the WT pair, indicating a low level of DSBs in the genome in the presence of the ZFN pairs containing the mutated FokI domains.

Example 5: Activity of the Engineered Half Domains in Primary Cells

Figure 10A:
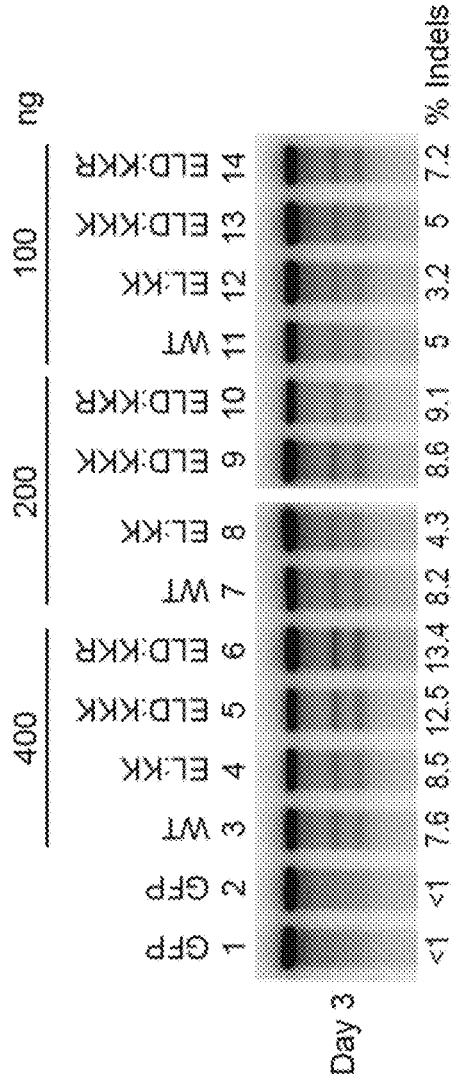
FIGS. 10A and 10B depict the activity of the novel ZFN mutants in primary cells.
Figure 10B:
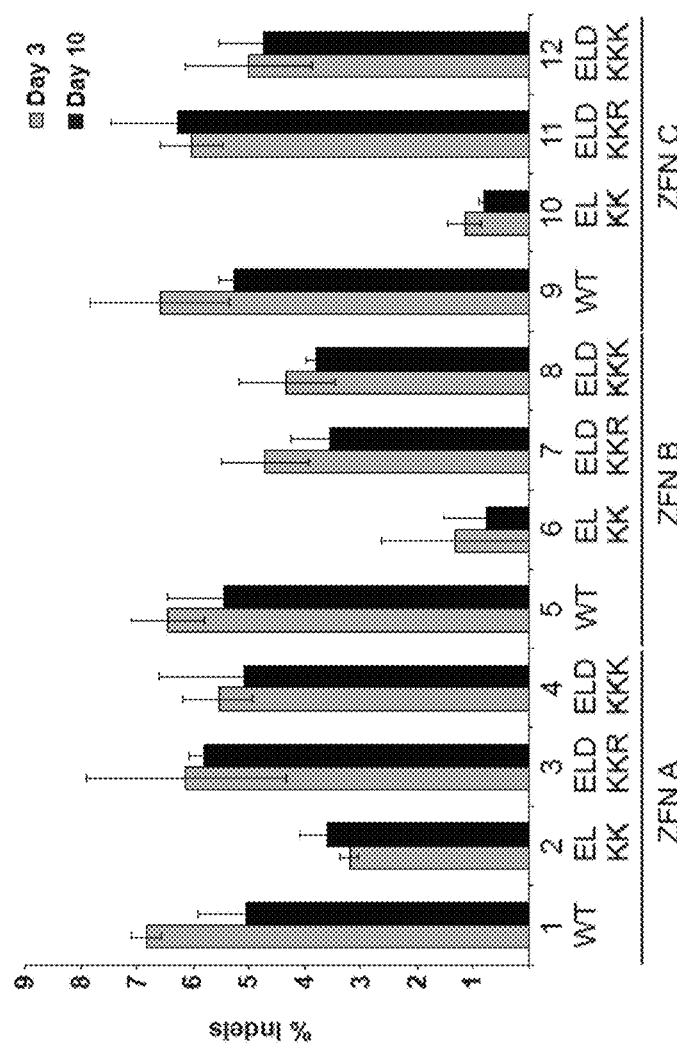

The constructs were also tested in primary cells. Decreasing amounts of CCR5-targeting ZFN constructs containing the indicated mutations were nucleofected in PBMCs, as described in Perez, et al., ibid. The cells were harvested three days post-transfection and the Cel-1 assay was used to determine the frequency of ZFN-induced indels. As can be seen from FIG. 10A, the ELD:KKK and ELD:KKR mutants were quite active in these cells even at lower concentrations. Similar studies were done with ZFNs targeted to PD-1 and are presented in FIG. 10B. Engineered half domain constructs were made in three pairs of PD-1-specific ZFNs where pair A comprised pair 12942 and 12974, pair B comprised pair 12942 and 25016, while pair C comprised pair 12942 and 25029 (see U.S. Provisional Application No. 61/281,432). The results are presented in FIG. 10B in a graphical format and demonstrate that the ELD:KKR and ELD:KKK mutants had superior activity as compared to both the WT pairs and the EL:KK pairs.

Figure 11A:
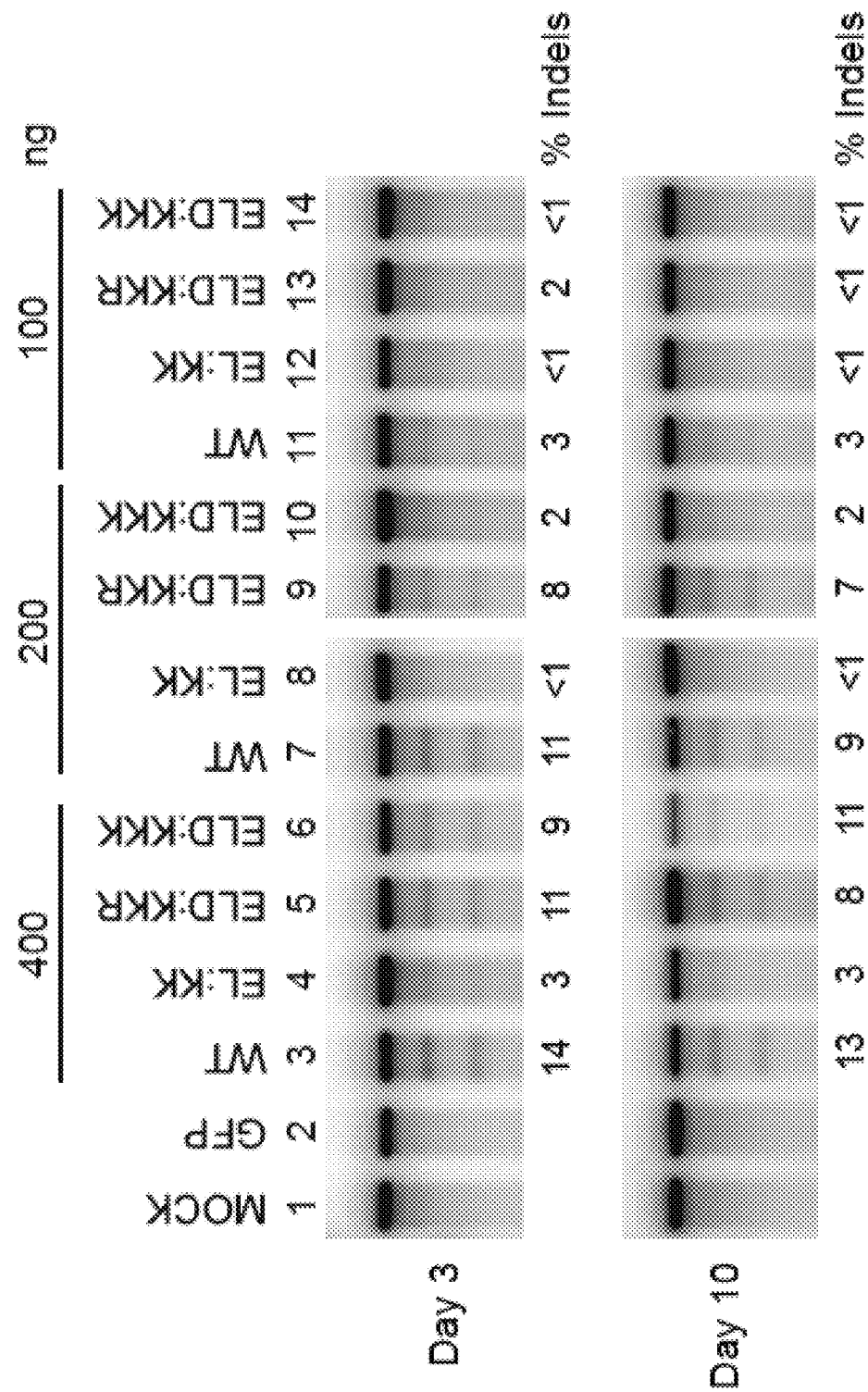

Mutants made in the GR-specific ZFN background were also tested in PBMCs for activity as shown in FIG. 11A. In this example, decreasing amounts of the mutants were tested at days 3 and 10 post-transfection. The new mutants were found to have increased activity as compared to the EL:KK pair. In FIG. 11B, the mean values of experiments that were repeated in six independent transfections in PBMC are presented. The values are mean+/−standard error of the mean of the relative activities as compared to the EL-KK pair. P-values use the two-sample T-test and demonstrate the reproducibility of these results.

Example 6: Targeted Integration into the DSB, Comparison of EL:KK and ELD:KKR

The EL:KK and ELD:KKR FokI mutant ZFNs were also compared for their use in promoting targeted integration (TI). For this experiment, a donor nucleic acid was made containing a novel BamHI restriction site. Following successful TI, the region surrounding the ZFN target site was amplified via PCR, and then the PCR product was subjected to BamHI restriction to cleave the newly introduced restriction site. The sequence of the donor DNA is shown below:

```
TI Donor DNA:
                                         (SEQ ID NO: 52)
ggaagttaaagcccatgtttctaatacaatgaacattatgttatgccca aacttaacaccatcatttcatatgatagcactttcttatagtgttacct tatgctccctgaccaaactcccagacatcaacttgtacttttctatttt attctagatattttgtattgttgttttaaatactttcctgcccattaga ggacctaggagccaccctectctcccctcttaactgatatttagcattc atgggattgcatataatggaaatttcaaaatccaccctgagaaatgaaa accaagtagaggaaaaataaactcttcaaaacacacactaccttccact gctcttttgaagaaaactttacagcttccacaagttaagactccataat gacatcctgaagcttcatcagagcacaccaggcagagtttgggagGTGG TCCTGTTGttgaggcatccagtccagacgggatccagccatactcactg ctGTTGAGGAGCTggatggaggagagcttacatctggtctcatgctggg gctaaagaagggaagaacagtgttatgatttaactgtcaaaggaatat caaaatacagttctcttagcttctcacttcatagtcagaatgctcacag tgaactctggcttcaagtgctagcaggcactaaaatatcctagctaaat atattcaaatcatgttatattcttctttaaacaaaattaagaatgaggt catttcttttgaagtgtctccaaaatagaatggtgtggttctggttcac ttatcttcttttttttttttttttttagatgataggatttattttataa tcacg
```

Figure 11C:
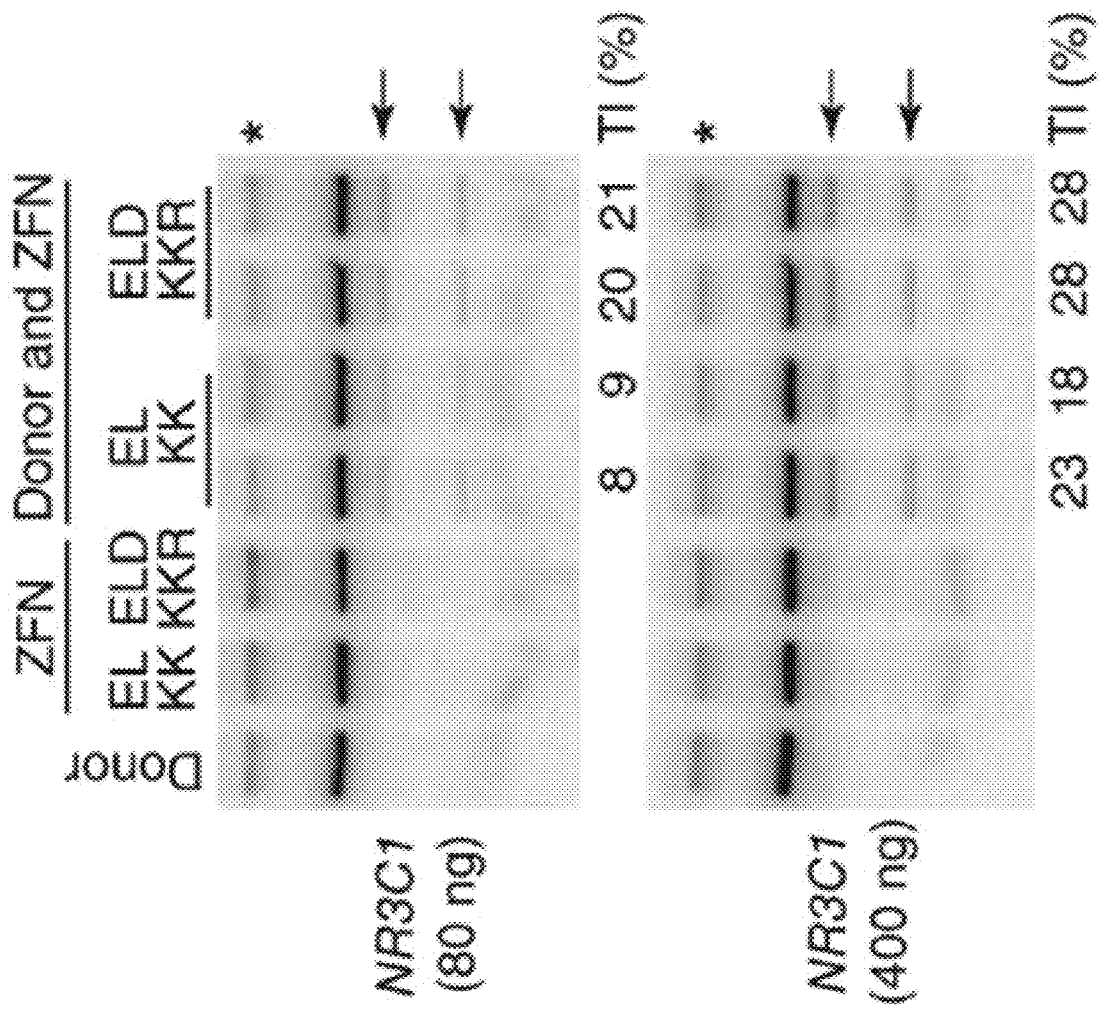

In this sequence, the ZFN binding sites are shown in capital letters, and the introduced BamHI restriction site is underlined. For these experiments, the FokI mutants were tested in the GR-specific ZFN background, and as shown in FIG. 11C, were done using two different ZFN-encoding plasmid concentrations during the nucleofection step. As can be seen in FIG. 11C, the ELD/KKR pair was more efficient at resulting in the introduction of the donor than the EL/KK pair, at both concentrations tested.

Example 7: Comparison of the Activity of DA:RV FokI Mutants Versus ELD:KKR or ELD:KKK ZFN pairs were constructed containing the FokI mutations in both the GR-specific and CCR5-specific ZFN backgrounds. These were then tested against their endogenous targets in K562 cells as described above, and assayed for cleavage activity using the Cel-I mismatch assay as described above. In each set of experiments, 80 ng of DNA encoding the ZFNs was used in the nucleofection step. At day 3 following transduction, the Cel-I assays were performed and the results are shown in FIG. 12, which shows the results for the GR-specific and CCR5-specific cleavage. The data demonstrates that the DA:RV FokI pair displayed much less activity than the EL:KK, ELD:KKK and ELD:KKR pairs. The EA:KV pair however showed activity in this assay.

Figure 13:
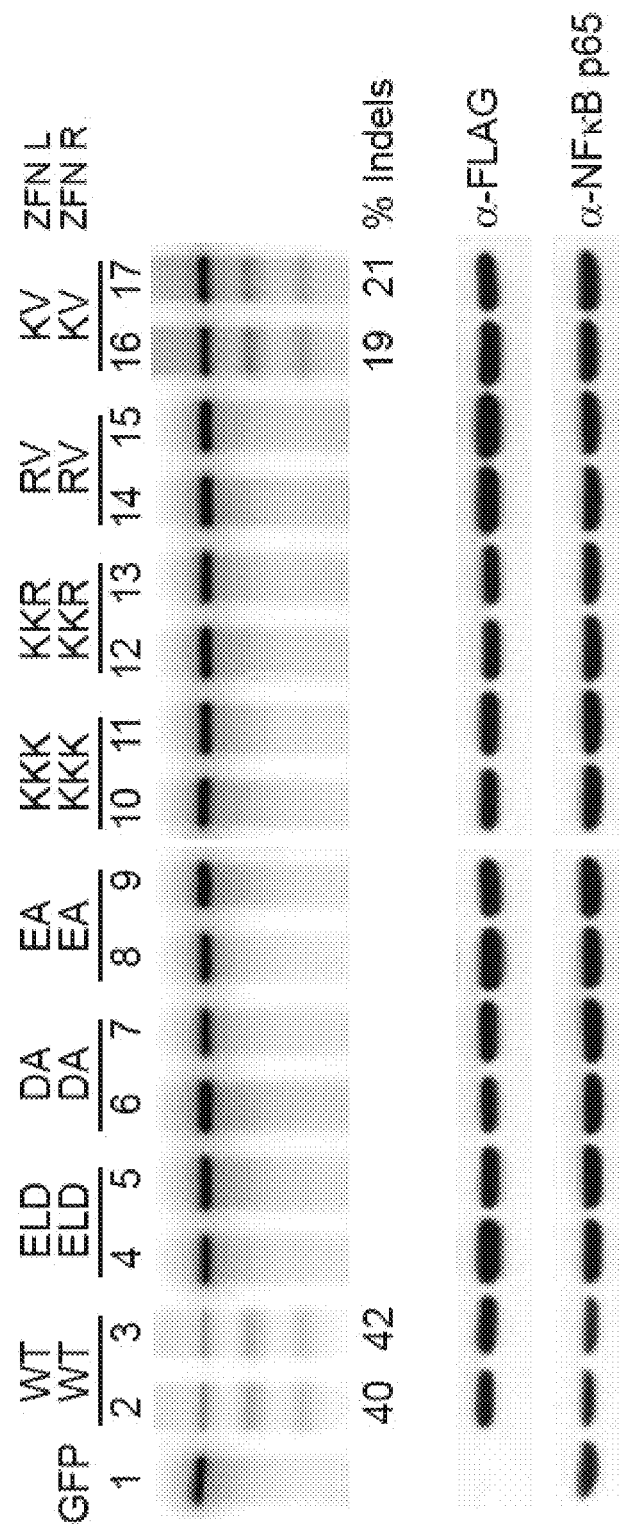
FIG. 13 depicts the activity observed when forced homodimerization of the FokI pairs is carried out. Activity is measured by the Cel-1 activity assay (as described above for FIG. 2). The ZFNs shown in FIG. 13 are specific for GR, and as can be seen from the Figure, the KV FokI mutant is the only one in this set to show appreciable homodimerization activity.

Next, the various ZFNs were tested for their ability to homodimerize by forced homodimerization (see Example 4). Typically, it is undesirable for two FokI mutant domains to have the ability to homodimerize because this may increase the potential for unwanted off target cleavage. The experiments were carried out as above except that 400 ng of ZFN containing plasmid were used for each nucleofection. The results are shown in FIG. 13 and demonstrate that the KV FokI mutant has the ability to homodimerize to a significant extent. Thus, although the EA:KV pair was found to have activity comparable to the ELD:KKR pair in this Cel-I assay (see FIG. 12), the fact that the KV FokI mutant was able to homodimerize and display cleavage activity makes it less desirable because of the increased risk of off-site cleavage.

Example 8: Enhancement of the Activity of the DA:RV FokI Mutants

Figure 14:
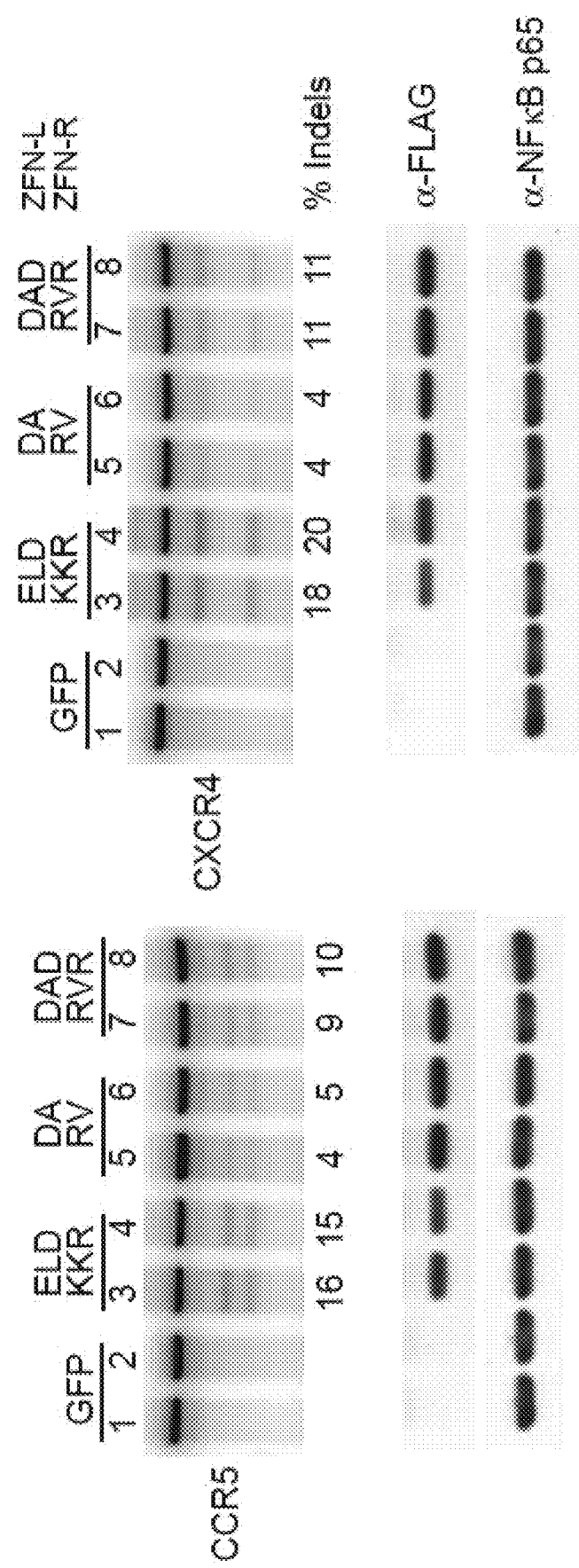
FIG. 14 depicts the activity as measured by the Cel-I activity assay (described above for FIG. 2) observed for the enhanced DA/RV pair which have been further modified with additional FokI mutations. The Figure depicts the results for both CCR5-specific and CXCR4-specific ZFN pairs wherein the FokI domain has been altered. As can be seen in the results, the additional mutation increases activity of the DA/RV mutant approximately 2 fold.

The DA:RV FokI mutants were then examined to see if it would be possible to increase their activity by combining them with other FokI mutations. Thus, the DA:RV pairs were made to include the N496D and H537R mutations resulting in a DAD:RVR pair. The Cel-I activity assay results for the CCR5-specific and CXCR4-specific pairs including these mutants are shown in FIG. 14. Experiments were carried out as previously described using 80 ng of plasmid per transduction. As can be seen from the Figure, the addition of the N496D and H537R mutations increased cleavage activity. Similar results were also found using these mutations in the GR-specific ZFN background (FIG. 14).

Figure 15:
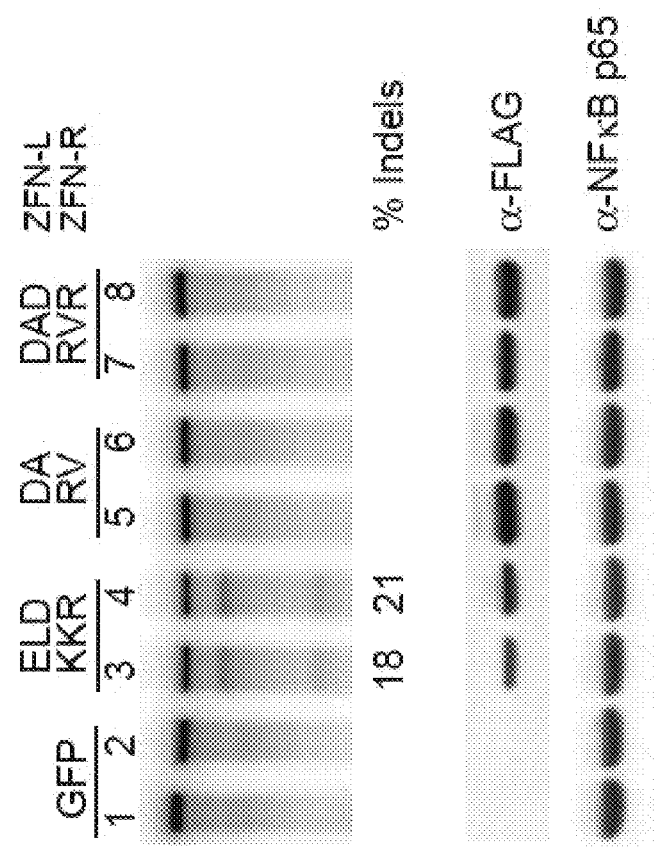
FIG. 15 depicts the Cel-I activity of the enhanced DA/RV pair DAD/RVR in a KDR-specific ZFN background. The KDR-specific ZFN pair has weaker activity to begin with, and the data demonstrate that the DAD/RVR mutant still does not have detectable activity in this assay and so is similar to the DA/RV pair. In comparison, the ELD/KKR KDR-specific ZFN FokI mutant pair shows activity (18-21% indels detected).

The DA:RV+N496D and H537R combination was also tested in a less active ZFN pair background. In this experiment, KDR-specific ZFNs were chosen and the results of the Cel-I assay are shown in FIG. 15. In this figure, the activity of both the DA:RV and DAD:RVR mutants were not detectable. Thus, the addition of the N496D and H537R mutations is helpful in some ZFNs but is not able to rescue ZFN pairs that have weak or undetectable activity.

Example 9: Testing of Orthogonal Pairs for Simultaneous Specific Dual Cleavage It may be desirable to perform simultaneous cleavage at two target sites within a genome. For added specificity, it would be best if only the ZFN pairs that cleave at the desired locus are able to productively dimerize such that an active pair has the specificity desired. To achieve this goal, pairs must not be able to homodimerize or transheterodimerize to create an active pair. In other words, if target 1 is cleaved by ZFN pair A+B, and target 2 is cleaved by ZFN pair X+Y, pairings of A+A (homodimers), A+X and A+Y (transheterodimers), for example, would be undesirable. Thus, the ELD/KKR+DAD/RVR pairs specific for CCR5 and CXCR4 were tested together with the hopes that the CCR5-specific ELD half cleavage domain would not be able to transheterodimerize with either the CXCR5-specific DAD or CXCR4-specific RVR half domains. In addition, variants of the ELD/KKR pair were made such that the D mutation at position 496 in the ELD mutant and the R mutation at position 537 in KKR were exchanged to form a REL/DKK pair (H537R+Q486E+I499L/N496D+E490K+I538K). In addition, the ELD/KKR+DD/RR pairs specific for CCR5 and CXCR4 were also tested together.

Figure 16:
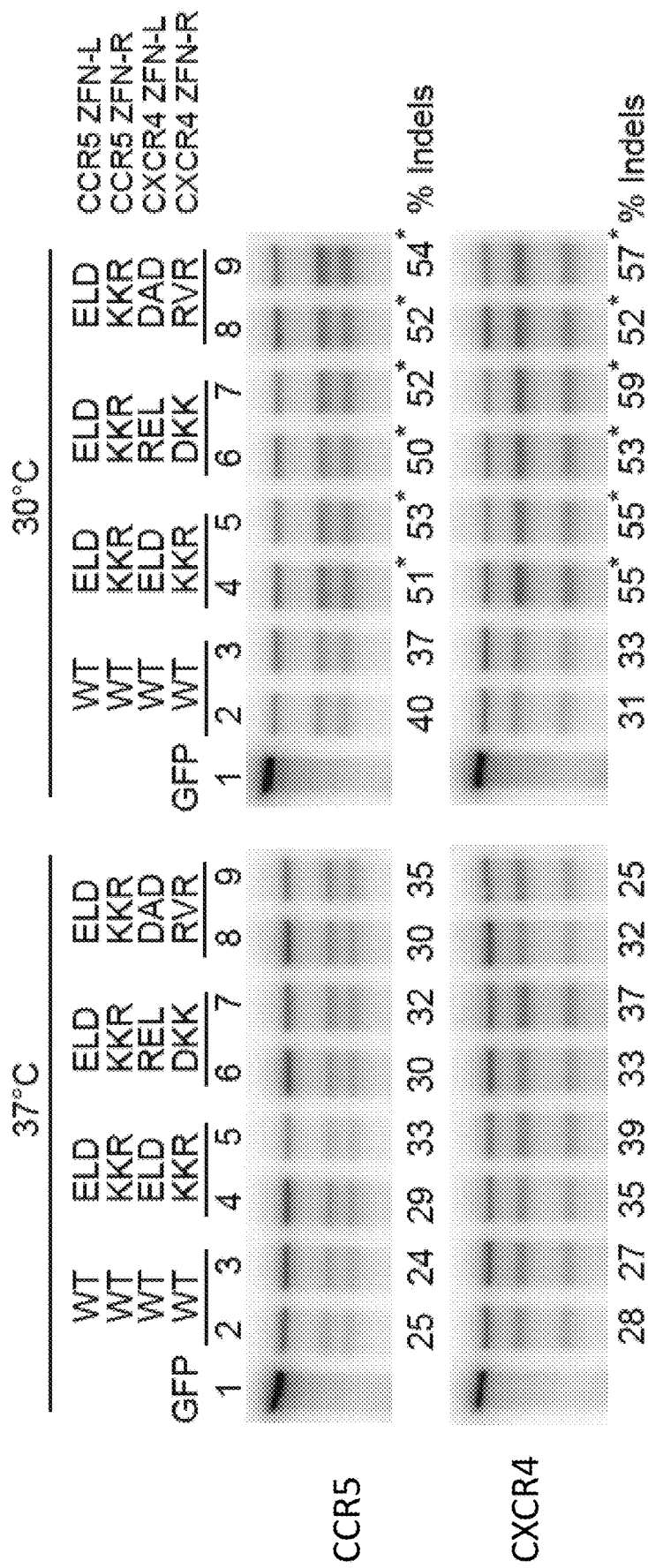
FIG. 16 depicts the results following nucleofection of the K562 cells with two sets of ZFN pairs, specific for CCR5 and CXCR4. The top panel shows the Cel-I assay results (as described above for FIG. 2) for the CCR5 target and the bottom panel shows similar results for the CXCR4 target. This experiment was carried out using two parallel incubation conditions, varying only in that one set was maintained only at 37° C. while the other set was held at 30° C. for 3 days. The figure shows that both pairs of ZFNs were active simultaneously.

The Cel-I activity assay results are shown in FIGS. 16 and 22. In this experiment, the conditions tested were both a standard 37° C. incubation as well as a 30° C. incubation (see co-owned U.S. Pat. No. 8,772,008). Briefly, following transduction, the cells were held at 37° C. for 3 days or at 30° C. for 3 days. Following incubation for 3 days, Cel-I assays were performed to see if both targets were cleaved, where the CCR5-specific Cel-I assay is shown on the top in FIG. 16, and the CXCR4-specific Cel-I assay is shown below.

These results indicate that cleavage at both the CCR5 and CXCR4 targets was achievable in a single step using these pairs of orthogonal mutants.

The mutants were further tested to examine potential off target cleavage. An in silico analysis was done to identify potential off target sites that might resemble a target that could be recognized by an illegitimate CCR5-CXCR4 transheterodimer ZFN pair. In these experiments, the four top candidates for off target cleavage were examined by the Cel-I assay, where the sequences for the off-target sites are listed below in Table 5.

TABLE 5

Potential Off-Target Sites

| Label | Pair | Locus | Target Sequence* |
|---|---|---|---|
| #3 | CCR5-L CXCR4-R | C1orf210 | CaTCATCCTCATCTTCAGCcACCTGTGGGcGG (SEQ ID NO: 53) |
| #5 | CCR5-L CXCR4-R | TBC1D5 | GGcaATaCTCATCTTCACTGACCTGaGGGTGG (SEQ ID NO: 54) |
| #7 | CCR5-R CXCR4-L | CD274 | ACtCCcCTaCTtCAACATAAACTGCAAAAGG (SEQ ID NO: 55) |

TABLE 5-continued

Potential Off-Target Sites

| Label | Pair | Locus | Target Sequence* |
|---|---|---|---|
| #10 | CCR5-R CXCR4-L | FRYL | AGACacCTTCaACTGCTTAAACTGaAAAAGG (SEQ ID NO: 56) |

Figure 17:
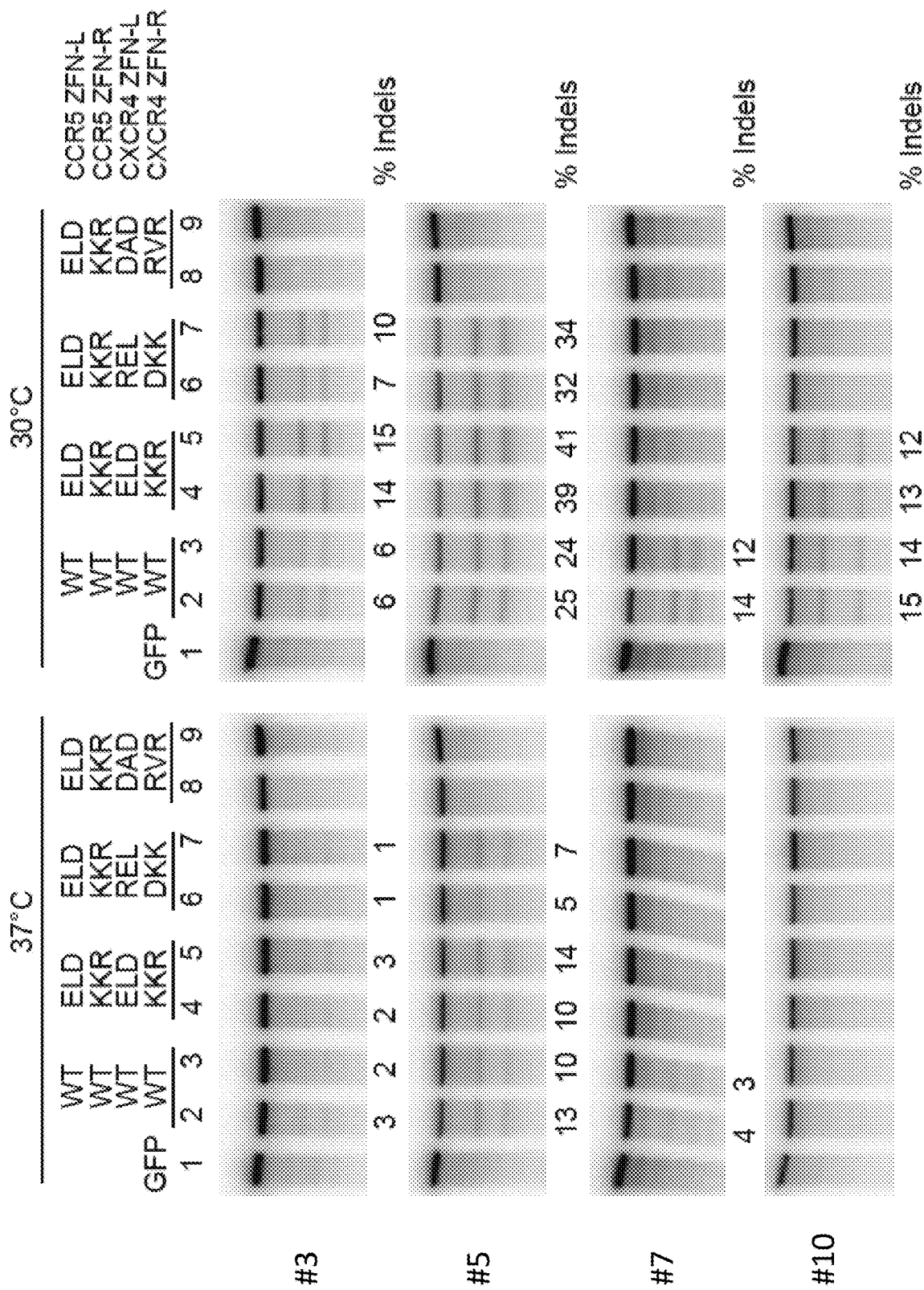
FIG. 17 depicts Cel-I assay cleavage results in K562 cells as above for FIG. 16 except that four potential off-target sites (#3, #5, #7 and #10) were analyzed for cleavage activity. The experiment was as above with two incubation conditions. The combination of the ELD/KKR-CCR5 FokI mutant pair with the DAD/RVR FokI mutant CXCR4 pair gave undetectable activity against these 4 off targets in this assay.

*Capital letters in the target sequence indicate potential contact points, lower case letters The transductions were tested as above using both the 37° C. and 30° C. incubation conditions, and the results are shown in FIGS. 17 and 22. As shown in FIG. 17, the ELD/KKR CCR5 pair in combination with the ELD/KKR CXCR4 pair gave some cleavage at off targets #3, #5 and #10. The ELD/KKR CCR5 pair combination with the REL/DKK CXCR4 pair also gave some cleavage at sites #3, #5 and #10. However, the ELD/KKR CCR5 pair, combined with the DAD/RVR CXCR4 pair gave no detectable cleavage at these off target sites. Furthermore, as shown in FIG. 22, the ELD/KKR CCR5 pair, combined with the DD/RR CXCR4 pair gave no detectable cleavage at these off target sites.

These results demonstrate that these FokI mutants may be used in sets to allow for simultaneous cleavage of more than one target site at a time, while decreasing undesirable off target cleavage.

Example 10: Evaluation of FokI Mutants Paired with the Sharkey Mutant

Figure 18:
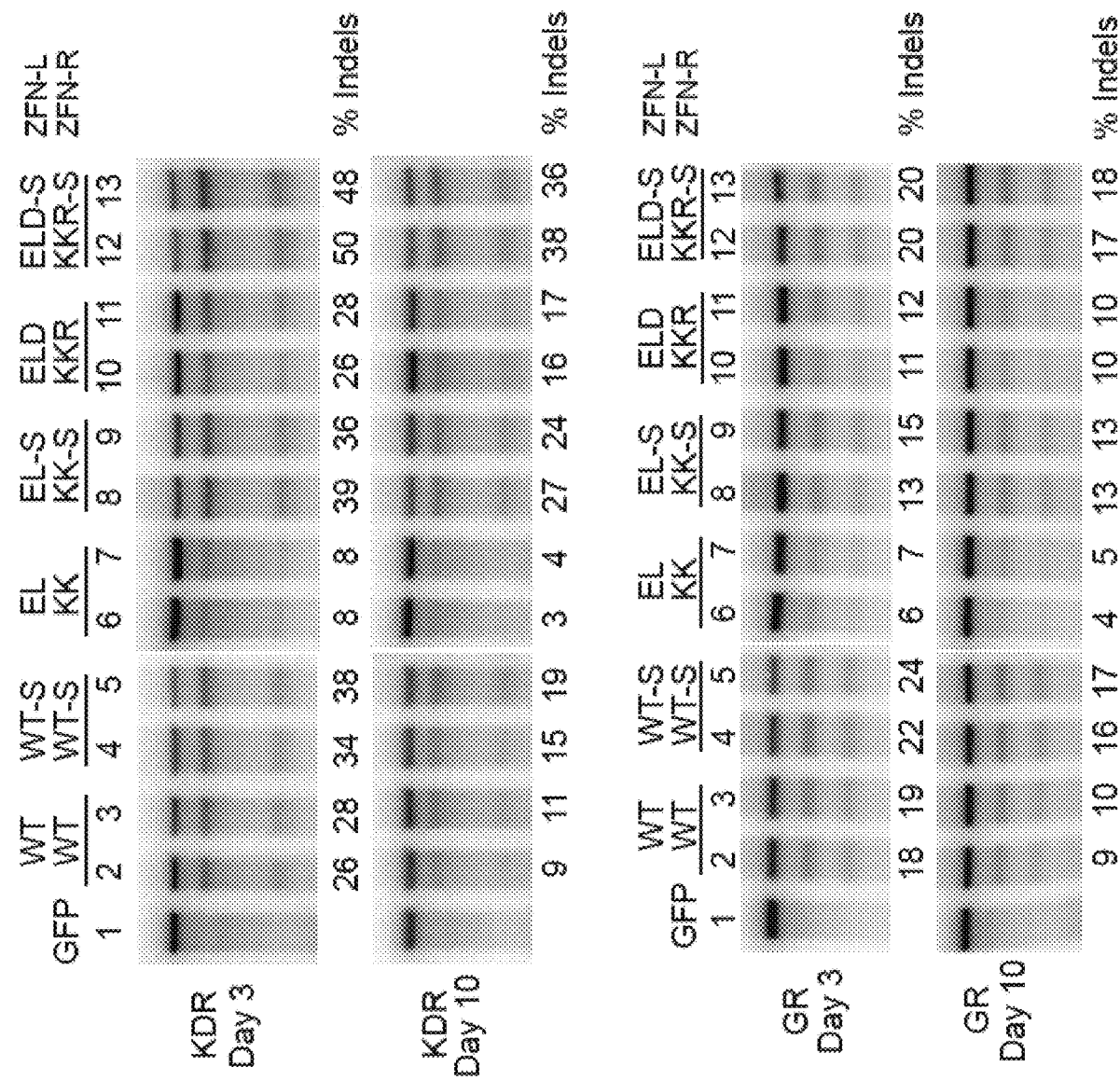
FIG. 18 depicts the results of the FokI mutants described in this invention in combination with the Sharkey mutant (see Table 4, and Guo et al., ibid) as assayed for activity using the Cel-I assay. The FokI mutant pairs tested were either specific for KDR (top panels) or GR (lower panels). The presence of the Sharkey mutation appears to increase the activity of the other FokI mutants.

A set of FokI mutants have been described which are thought to enhance efficiency of DNA cleavage (see Guo, et al., ibid), which are known as the Sharkey (S418P+K441E) and Sharkey' (S418P+F432L+K441E+Q481H+H523Y+N527D+K559Q) FokI mutants. Thus, the Sharkey mutant was tested in combination with the various FokI mutants described herein to see if cleavage activity could be further enhanced by the presence of the Sharkey mutations. The mutant combinations were made in the GR-specific and the KDR-specific ZFN backgrounds and tested for cleavage activity using the Cel-I assay as described above. The results are shown in FIG. 18, and demonstrate that the activities of the mutations appear to be additive. For example, comparison of lanes 10 and 11 with lanes 12 and 13 on the day 3 panel shows that the detected NHEJ activity (indels) went from 11-12 for the ELD/KKR GR-specific pair to 20% indels for the ELD-S/KKR-S pair. Similarly, comparison of lanes 10 and 11 with lanes 12 and 13 for the KDR specific ZFNs at day 3 went from approximately 26-28% indels detectable to 48-50% indels detectable.

Figure 19A:
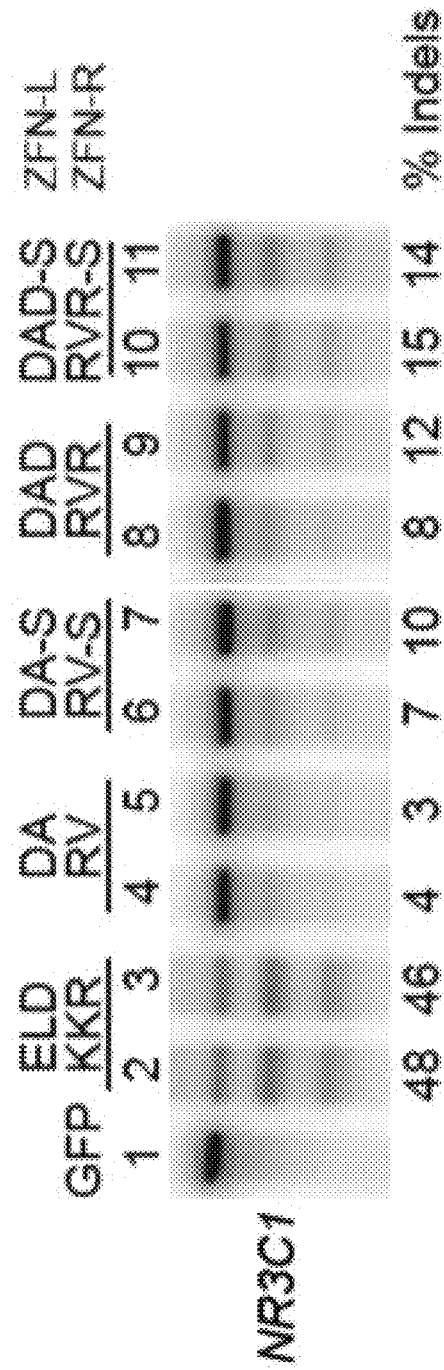
FIGS. 19A and 19B depict the activity results of the FokI mutants described in this invention in combination with the Sharkey mutant (see Table 4, and Guo et al., ibid) as assayed for activity using the Cel-I assay. The ZFN FokI mutant pairs tested were specific for GR. The presence of the Sharkey mutation appears to increase the activity of the other FokI mutants.
Figure 19B:
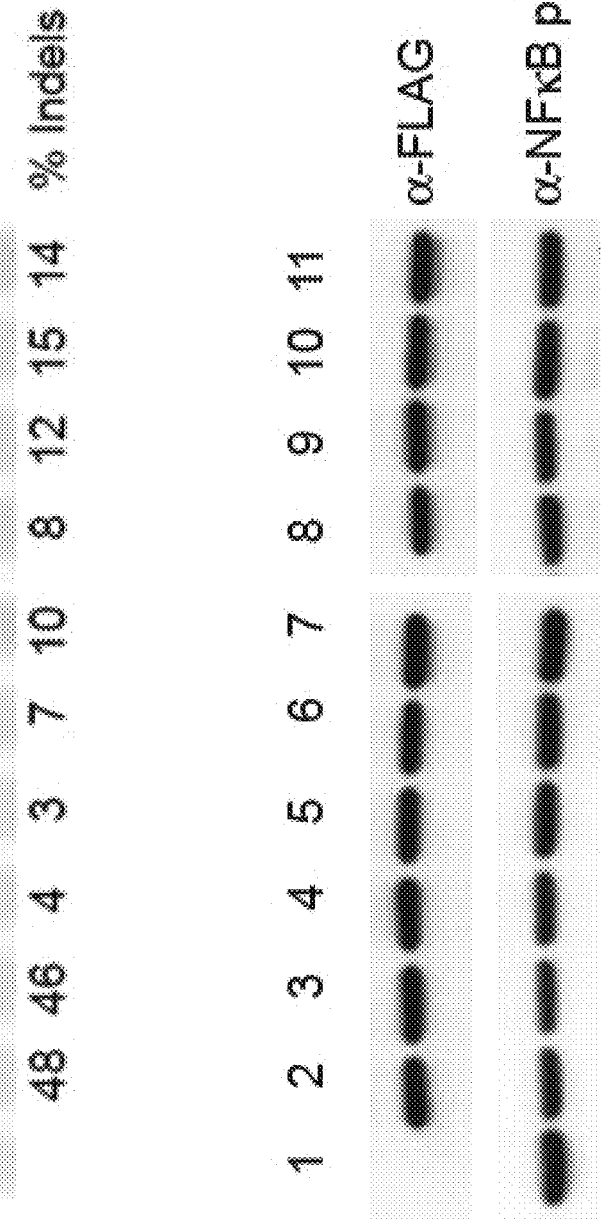

In addition, Sharkey FokI mutants were also combined with the DA/RV and DAD/RVR FokI mutants in the GR-specific ZFN background, and tested for activity using the Cel-I activity assay. The results are presented in FIG. 19A and show that the FokI mutations are additive in terms of activity. (Compare lanes 4 and 5 with lanes 6 and 7).

Figures 20A, 20B:
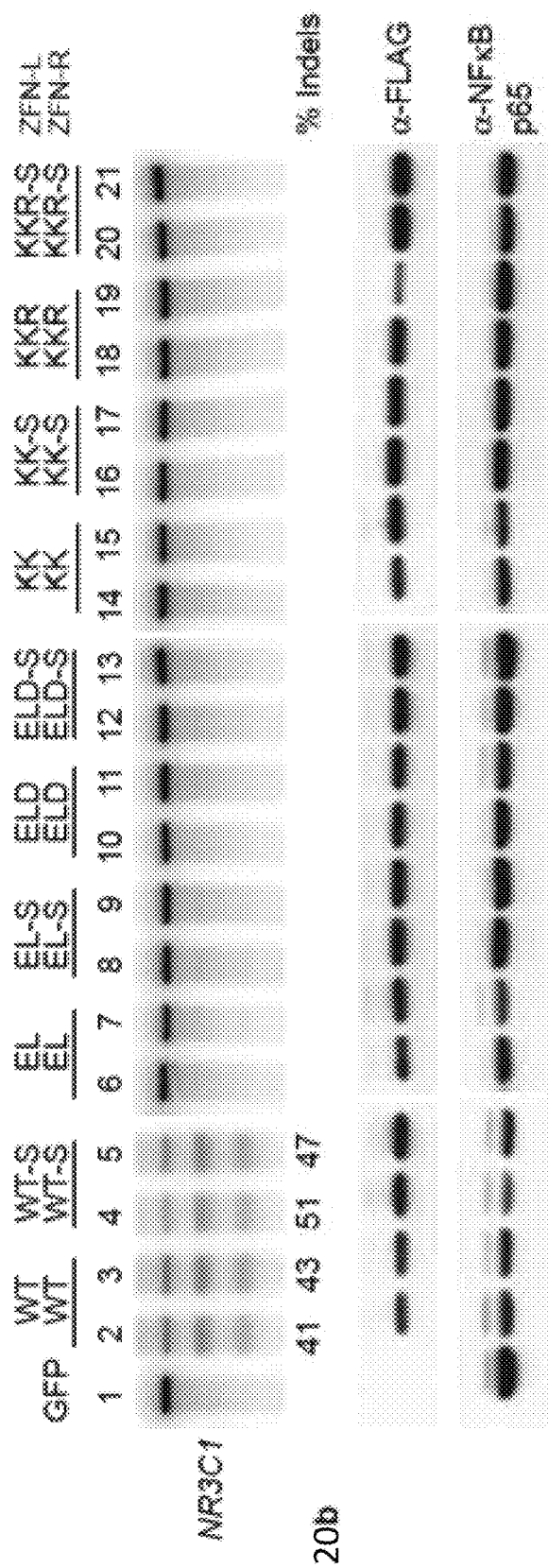
FIGS. 20A through 20D depict activity results of various FokI mutant+Sharkey FokI mutants are forced to homodimerize as assayed by the Cel-I assay. As shown, FokI mutants do not form active homodimer complexes.
Figures 20C, 20D:
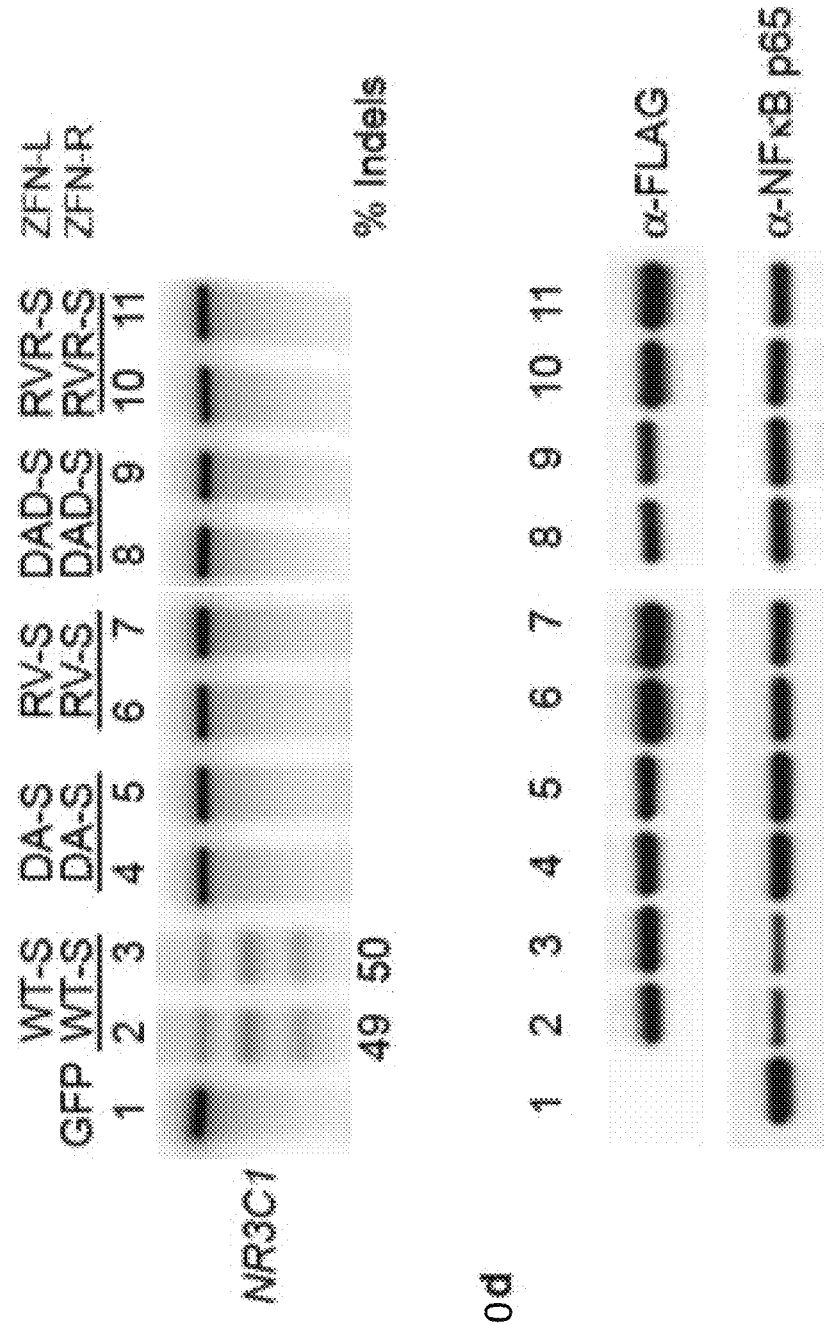
Figure 21A:
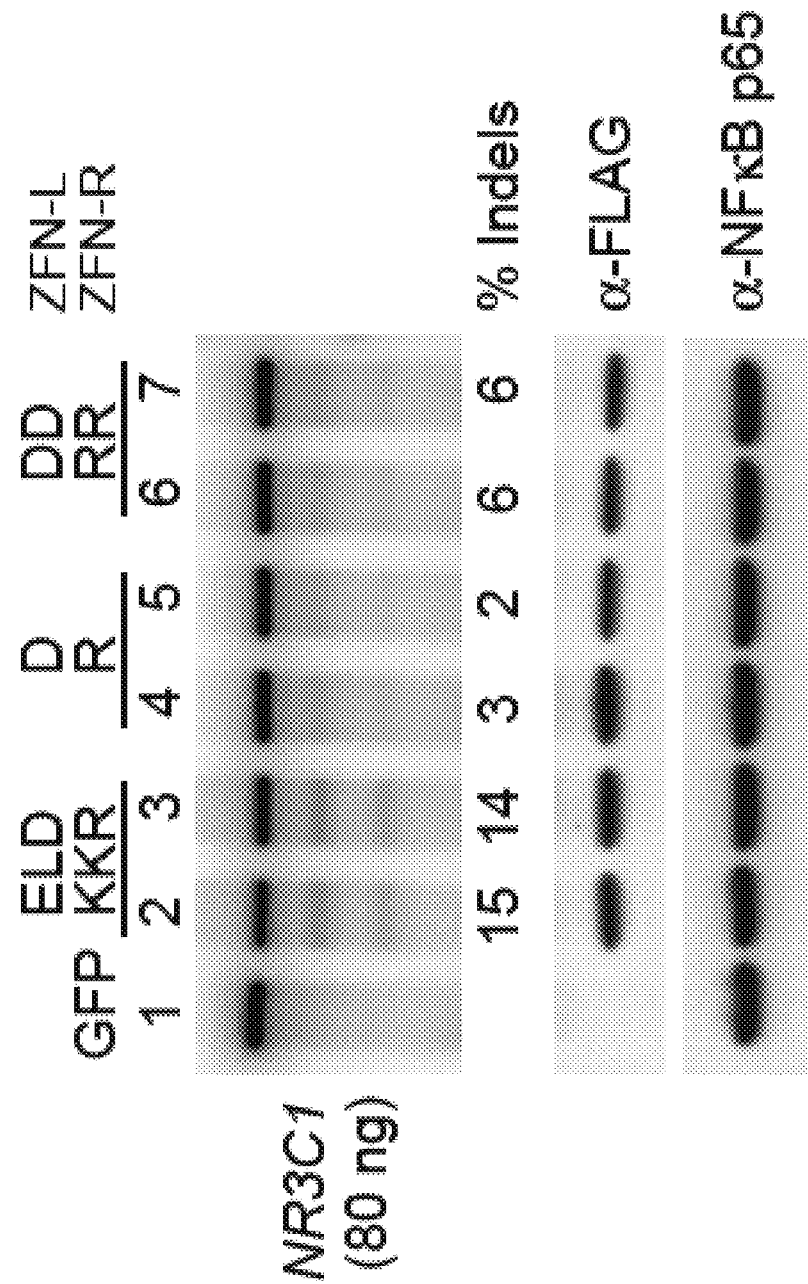
FIGS. 21A and 21B depict activity results of D:R and DD:RR FokI mutants in the context of the indicated ZFNs as assayed by Cel-I assay.
Figure 21B:
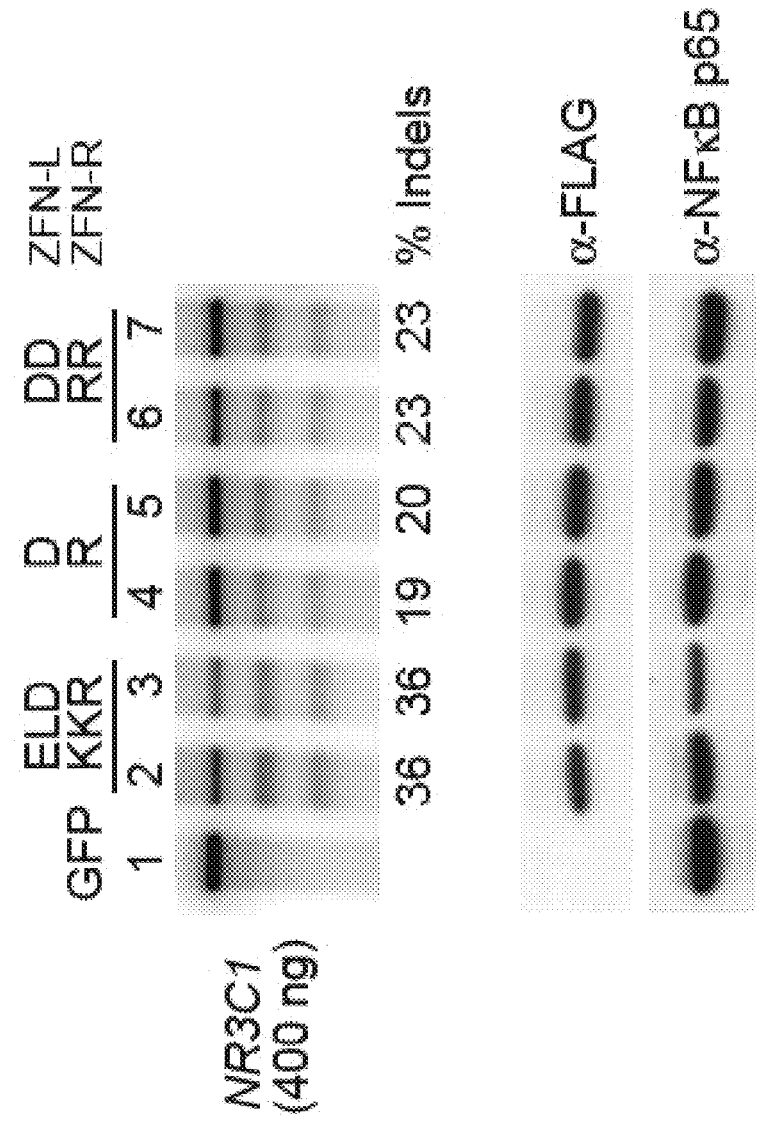

The mutant combinations were also tested to see if the presence of the Sharkey mutation increased the amount of homodimerization cleavage in a forced homodimerization assay as described above in Example 4. FIG. 20 shows the results of the GR-specific mutants, with or without the added Sharkey mutation. As can be seen from the figure, the mutants were not detectably altered in the homodimerization capability. Similarly, the DA-S/RV-S and DAD-S/RVR-S mutants were also tested to see if there was an increase in homodimerization in the GR-specific ZFN background. The results are shown in FIG. 21A, and demonstrate that there was not an increase in productive homodimerization. FIG. 21B demonstrates an equal loading of all lanes.

Example 11: Enhancement of the Activity of the D:R FokI Mutants

The D:R FokI mutants (R487D:D483R) (see, e.g., U.S. Patent Publication Nos. 2008/0131962 and 2009/0305346) were examined to see if it would be possible to increase their activity by combining them with other FokI mutations. Briefly, the D:R pairs were made to include the N496D and H537R mutations resulting in a DD:RR pair and Cel-I assays performed as described above.

As shown in FIG. 21, the addition of the N496D and H537R mutations increased cleavage activity.

In sum, these results demonstrate that FokI mutants described herein are the data presented here demonstrate that the novel mutants are more active and display less off-site cleavage activity than the previously described FokI mutants.

What is claimed is:

1. An artificial nuclease comprising:
   (i) a DNA-binding domain that binds to a target site in the genome of the cell; and
   (ii) a polypeptide comprising an engineered FokI cleavage half-domain, wherein the engineered cleavage half-domain comprises substitution mutations selected from the group consisting of:
   substitution mutations at amino acid residues 486, 499 and 496;
   substitution mutations at amino acid residues 487 and 496;
   substitution mutations at amino acid residues 487, 499, and 496;
   substitution mutations at amino acid residues 483 and 537;
   substitution mutations at amino acid residues 490 and 537;
   substitution mutations at amino acid residues 490, 537 and 538;
   substitution mutations at amino acid residues 483, 496 and 537;
   substitution mutations at amino acid positions 487, 496 and 537;
   substitution mutations at amino acid residues 487, 499 and 496; and
   substitution mutations at amino acid residues 483, 537 and 538;
   wherein the amino acid residues are numbered relative to full length wild-type FokI as shown in SEQ ID NO: 57.

2. A method of making a genomic modification in a cell, the method comprising administering at least one artificial nuclease according to claim 1 to a cell, wherein the artificial nuclease genetically modifies a gene locus in the cell.

3. The method of claim 2, wherein the gene locus is inactivated.

4. The method of claim 2, wherein the genomic modification comprises an insertion.

5. The method of claim 4, wherein a transgene is inserted into the gene locus.

6. The method of claim 2, wherein the genomic modification comprises a deletion.

7. The method of claim 6, wherein the genomic modification further comprises an insertion.

8. The method of claim 7, wherein a transgene is inserted into the gene locus.

9. The method of claim 2, wherein the cell is a T-cell, a hematopoietic stem cell or a liver cell.

10. The artificial nuclease of claim 1, wherein the engineered cleavage half-domain comprises substitution mutations at amino acid residues 486, 499 and 496 and further wherein the wild-type Gln (Q) residue at position 486 is replaced with a Glu (E) residue, the wild-type Iso (I) residue at position 499 is replaced with a Leu (L) residue and the wild-type Asn (N) residue at position 496 is replaced with an Asp (D) or a Glu (E) residue.

11. The artificial nuclease of claim 1, wherein the engineered cleavage half-domain comprises substitution mutations at amino acid residues 490, 538 and 537 and further wherein the wild-type Glu (E) residue at position 490 is replaced with a Lys (K) residue, the wild-type Iso (I) residue at position 538 is replaced with a Lys (K) residue, and the wild-type His (H) residue at position 537 is replaced with a Lys (K) residue or a Arg (R) residue.

12. The artificial nuclease of claim 1, wherein the engineered cleavage half-domain comprises substitution mutations at amino acid residues 490 and 537 and further wherein the wild-type Glu (E) residue at position 490 is replaced with a Lys (K) residue and the wild-type His (H) residue at position 537 is replaced with a Lys (K) residue or a Arg (R) residue.

13. The artificial nuclease of claim 1, wherein the engineered cleavage half-domain comprises substitution mutations at amino acid residues 487 and 496 and further wherein the wild-type Arg (R) residue at position 487 is replaced with an Asp (D) residue- and the wild-type Asn (N) residue at position 496 is replaced with an Asp (D) residue.

14. The nuclease of claim 13, further wherein the wild-type Ile (I) residue at position 499 is replaced with an Ala (A).

15. The artificial nuclease of claim 1, wherein the engineered cleavage half-domain comprises substitution mutations at amino acid residues 483 and 537 and further wherein the wild-type Asp (D) residue at position 483 is replaced with an Arg (R) residue and the wild-type His (H) residue at position 537 is replaced with an Arg (R) residue.

16. The artificial nuclease of claim 1, wherein the engineered cleavage half-domain comprises substitution mutations at amino acid residues 487, 496 and 537 and further wherein the wild-type Arg (R) residue at position 487 is replaced with an Asp (D) residue, the wild-type Asn (N) residue at position 496 is replaced with an Asp (D) residue and the wild-type His (H) residue at position 537 is replaced with an Arg (R) residue.

17. The artificial nuclease of claim 1, wherein the engineered cleavage half-domain comprises substitution mutations at amino acid residues 483, 496 and 537 and further wherein the wild-type Asp (D) residue at position 483 is replaced with an Arg (R) residue, the wild-type Asn (N) residue at position 496 is replaced with an Asp (D) residue and the wild-type His (H) residue at position 537 is replaced with an Arg (R) residue.

18. The artificial nuclease of claim 1, further comprising an additional amino acid substitution at one or more of positions 418, 432, 441, 481, 483, 486, 487, 490, 496, 499, 523, 527, 537, 538 and 559.

* * * * *

SEQUENCE LISTING

<160> NUMBER OF SEQ ID NOS: 57

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Arg Ser Asp His Leu Ser Thr
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ser Ala Asn Leu Ser Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ser Asp Asn Leu Ser Glu
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Ser Gly Ser Leu Thr Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ser Gly Ala Leu Ala Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Asp Asn Leu Thr Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 7

Gln Ser Gly Asn Leu Ala Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ser Gly His Leu Gln Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Ser Asp Leu Arg Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp Thr Leu Ser Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ser Asp Asn Leu Ser Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Asn Ala His Arg Thr Thr
1               5

<210> SEQ ID NO 13
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Gln Ser Ser Asn Leu Ala Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Asp Asp Leu Thr Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Arg Ser His Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Asn Pro Asn Leu Asn Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Asp Asp Leu Ser Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Asn Ala His Arg Ile Asn
1               5
```

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Ala Asn Leu Thr Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ser Lys Thr Arg Lys Asn
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Arg Ser Asn Leu Ser Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Asp His Leu Ser Ala
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Ser Gly His Leu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Ser Gly Ser Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Asp Thr Leu Ser Ala
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Asn Ser Asn Arg Ile Lys
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ser Ala Ala Leu Ser Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Gly Asp Leu Thr Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Asp Ser Leu Ser Ala
1               5

<210> SEQ ID NO 30
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Arg Ser Asn Leu Thr Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ser Asp Asn Leu Ser Gln
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Ser Asn Asp Arg Lys Lys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Ser Ser Thr Arg Lys Lys
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ser Asp Asn Leu Ser Val
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Arg Ser His Leu Ala Arg
```

```
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Arg Ser Asn Leu Val Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ser Ser Asp Leu Thr Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Asn Val Asp Leu Ile Glu
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser Ser Asn Leu Ser Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ser Asp Ser Leu Ser Val
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 41

Thr Asn His Asn Arg Lys Thr
1               5

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ttgttcagga ttggacacaa catcctag                                         28

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cagctggaga agaacgagga gacggtaa                                         28

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctgcggatag tgaggttccg gttcccat                                         28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tgaggaagga ggacgaaggc ctctacac                                         28

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
atgatgacgc ccaggagctt caccaccc                                         28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 47
gaggaaggga agtactccct ggtgatgg                                                28

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gtgcagtgaa ccaggctgtt ctgtggct                                                28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gttcccaggg acttgggatg ggtcctgt                                                28

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aaggaggcaa ggccgaggtc tgcgatct                                                28

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aagatgtgga gcaaactgaa taatgaag                                                28

<210> SEQ ID NO 52
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
ggaagttaaa gcccatgttt ctaatacaat gaacattatg ttatgcccaa acttaacacc            60
atcatttcat atgatagcac tttcttatag tgttacctta tgctccctga ccaaactccc           120
agacatcaac ttgtactttt ctattttatt ctagatcttt ttgtattgtt gttttaaata           180
ctttcctgcc cattagagga cctaggagcc accctcctct ccctcttaa ctgatattta            240 gcctttcatg ggctttgcat ataatggaaa tttcaaaatc caccctgaga aatgaaaacc           300

-continued

```
aagtagagga aaaataaact cttcaaaaca cacactacct tccactgctc ttttgaagaa    360
aactttacag cttccacaag ttaagactcc ataatgacat cctgaagctt catcagagca    420
caccaggcag agtttgggag gtggtcctgt tgttgaggca tccagtccag acgggatcca    480
gccatactca ctgctgttga ggagctggat ggaggagagc ttacatctgg tctcatgctg    540
gggctaaaga aggggaagaa cagtgttatg atttaactgt caaaggaata tcaaaataca    600
gttctcttag cttctcactt catagtcaga atgctcacag tgaactctgg cttcaagtgc    660
tagcaggcac taaaatatcc tagctaaata tattcaaatc atgttatatt cttctttaaa    720
caaaattaag aatgaggtca tttcttttga agtgtctcca aaatagaatg gtgtggttct    780
ggttcacttc ttcttctttt tttttttttt tttagatgct taggatttat ttttataatc    840
acg                                                                 843
```

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
catcatcctc atcttcagcc acctgtgggc gg                                  32

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggcaatactc atcttcactg acctgagggt gg                                  32

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
actcccctac ttcaacataa actgcaaaag g                                   31

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agacaccttc aactgcttaa actgaaaaag g                                   31

<210> SEQ ID NO 57
<211> LENGTH: 579
<212> TYPE: PRT
<213> ORGANISM: Flavobacterium okeanokoites
<220> FEATURE:
<223> OTHER INFORMATION: FokI sequence

<400> SEQUENCE: 57

Met Val Ser Lys Ile Arg Thr Phe Gly Trp Val Gln Asn Pro Gly Lys
1               5                   10                  15

Phe Glu Asn Leu Lys Arg Val Val Gln Val Phe Asp Arg Asn Ser Lys
            20                  25                  30

Val His Asn Glu Val Lys Asn Ile Lys Ile Pro Thr Leu Val Lys Glu
        35                  40                  45

Ser Lys Ile Gln Lys Glu Leu Val Ala Ile Met Asn Gln His Asp Leu
50                  55                  60

Ile Tyr Thr Tyr Lys Glu Leu Val Gly Thr Gly Thr Ser Ile Arg Ser
65                  70                  75                  80

Glu Ala Pro Cys Asp Ala Ile Ile Gln Ala Thr Ile Ala Asp Gln Gly
                85                  90                  95

Asn Lys Lys Gly Tyr Ile Asp Asn Trp Ser Ser Asp Gly Phe Leu Arg
            100                 105                 110

Trp Ala His Ala Leu Gly Phe Ile Glu Tyr Ile Asn Lys Ser Asp Ser
        115                 120                 125

Phe Val Ile Thr Asp Val Gly Leu Ala Tyr Ser Lys Ser Ala Asp Gly
130                 135                 140

Ser Ala Ile Glu Lys Glu Ile Leu Ile Glu Ala Ile Ser Ser Tyr Pro
145                 150                 155                 160

Pro Ala Ile Arg Ile Leu Thr Leu Leu Glu Asp Gly Gln His Leu Thr
                165                 170                 175

Lys Phe Asp Leu Gly Lys Asn Leu Gly Phe Ser Gly Glu Ser Gly Phe
            180                 185                 190

Thr Ser Leu Pro Glu Gly Ile Leu Leu Asp Thr Leu Ala Asn Ala Met
        195                 200                 205

Pro Lys Asp Lys Gly Glu Ile Arg Asn Asn Trp Glu Gly Ser Ser Asp
210                 215                 220

Lys Tyr Ala Arg Met Ile Gly Gly Trp Leu Asp Lys Leu Gly Leu Val
225                 230                 235                 240

Lys Gln Gly Lys Lys Glu Phe Ile Ile Pro Thr Leu Gly Lys Pro Asp
                245                 250                 255

Asn Lys Glu Phe Ile Ser His Ala Phe Lys Ile Thr Gly Glu Gly Leu
            260                 265                 270

Lys Val Leu Arg Arg Ala Lys Gly Ser Thr Lys Phe Thr Arg Val Pro
        275                 280                 285

Lys Arg Val Tyr Trp Glu Met Leu Ala Thr Asn Leu Thr Asp Lys Glu
290                 295                 300

Tyr Val Arg Thr Arg Arg Ala Leu Ile Leu Glu Ile Leu Ile Lys Ala
305                 310                 315                 320

Gly Ser Leu Lys Ile Glu Gln Ile Gln Asp Asn Leu Lys Lys Leu Gly
                325                 330                 335

Phe Asp Glu Val Ile Glu Thr Ile Glu Asn Asp Ile Lys Gly Leu Ile
            340                 345                 350

Asn Thr Gly Ile Phe Ile Glu Ile Lys Gly Arg Phe Tyr Gln Leu Lys
        355                 360                 365

Asp His Ile Leu Gln Phe Val Ile Pro Asn Arg Leu Gly Lys Pro Asp
370                 375                 380

Leu Val Lys Ser Glu Leu Glu Glu Lys Ser Glu Leu Arg His Lys
385                 390                 395                 400

Leu Lys Tyr Val Pro His Glu Tyr Ile Glu Leu Ile Glu Ile Ala Arg

-continued

```
                405                 410                 415
Asn Ser Thr Gln Asp Arg Ile Leu Glu Met Lys Val Met Glu Phe Phe
            420                 425                 430

Met Lys Val Tyr Gly Tyr Arg Gly Lys His Leu Gly Gly Ser Arg Lys
        435                 440                 445

Pro Asp Gly Ala Ile Tyr Thr Val Gly Ser Pro Ile Asp Tyr Gly Val
    450                 455                 460

Ile Val Asp Thr Lys Ala Tyr Ser Gly Gly Tyr Asn Leu Pro Ile Gly
465                 470                 475                 480

Gln Ala Asp Glu Met Gln Arg Tyr Val Glu Glu Asn Gln Thr Arg Asn
                485                 490                 495

Lys His Ile Asn Pro Asn Glu Trp Trp Lys Val Tyr Pro Ser Ser Val
            500                 505                 510

Thr Glu Phe Lys Phe Leu Phe Val Ser Gly His Phe Lys Gly Asn Tyr
        515                 520                 525

Lys Ala Gln Leu Thr Arg Leu Asn His Ile Thr Asn Cys Asn Gly Ala
    530                 535                 540

Val Leu Ser Val Glu Glu Leu Leu Ile Gly Gly Glu Met Ile Lys Ala
545                 550                 555                 560

Gly Thr Leu Thr Leu Glu Glu Val Arg Arg Lys Phe Asn Asn Gly Glu
                565                 570                 575

Ile Asn Phe
```